United States Patent [19]
Kwan

[11] Patent Number: 6,068,479
[45] Date of Patent: May 30, 2000

[54] DENTAL IMPLANT SYSTEM

[76] Inventor: Norman Ho-Kwong Kwan, 209 Indian Valley Trail, Mississauga, Ontario, Canada, L5G 2K5

[21] Appl. No.: 09/028,007

[22] Filed: Feb. 23, 1998

Related U.S. Application Data

[63] Continuation-in-part of application No. 08/654,315, May 28, 1996, Pat. No. 5,733,124, which is a continuation-in-part of application No. 08/391,662, Feb. 21, 1995, Pat. No. 5,564,924.

[51] Int. Cl.[7] ........................................ A61C 8/00
[52] U.S. Cl. ................................................ 433/173
[58] Field of Search ............................... 433/172, 173, 433/174, 175, 176

[56] References Cited

U.S. PATENT DOCUMENTS

| | | | |
|---|---|---|---|
| 5,439,380 | 8/1995 | Marlin | 433/172 |
| 5,564,924 | 10/1996 | Kwan | 433/173 |
| 5,688,123 | 11/1997 | Meiers et al. | 433/172 X |
| 5,704,788 | 1/1998 | Milne | 433/172 X |
| 5,733,124 | 3/1998 | Kwan | 433/173 |
| 5,759,036 | 6/1998 | Hinds | 433/172 X |
| 5,782,918 | 7/1998 | Klardie et al. | 433/172 X |
| 5,816,809 | 10/1998 | Sapkos | 433/172 |
| 5,829,977 | 11/1998 | Rogers et al. | 433/173 X |

*Primary Examiner*—Nicholas D. Lucchesi
*Attorney, Agent, or Firm*—Howard J. Greenwald

[57] ABSTRACT

A dental implant assembly containing an integral dental implant which has an abutment integrally joined to a implant fixture. The abutment contains a top section, a bottom section integrally joined to the top section, and an orifice extending through a portion of the top section. The top section has a cross-sectional shape substantially like a polygon which is formed by alternating linear and arcuate walls. The abutment also has a ledge disposed beneath the top section of said abutment.

14 Claims, 37 Drawing Sheets

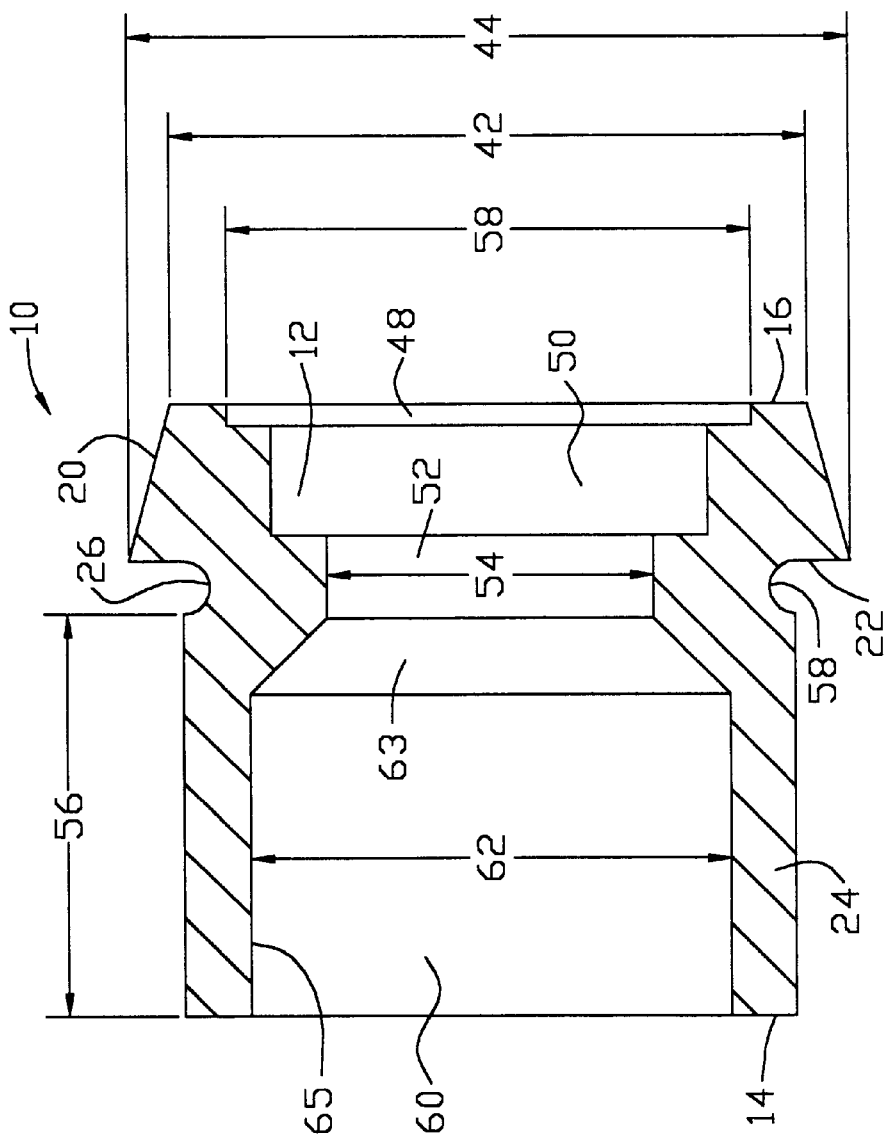

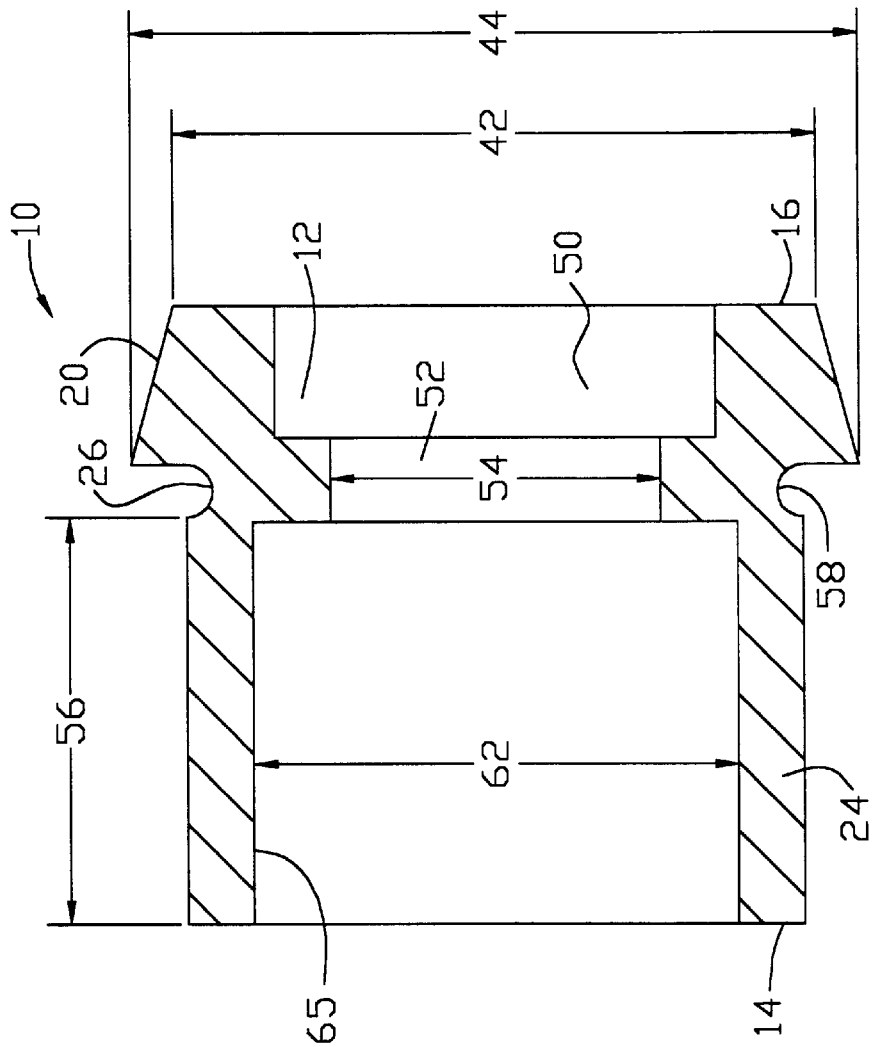

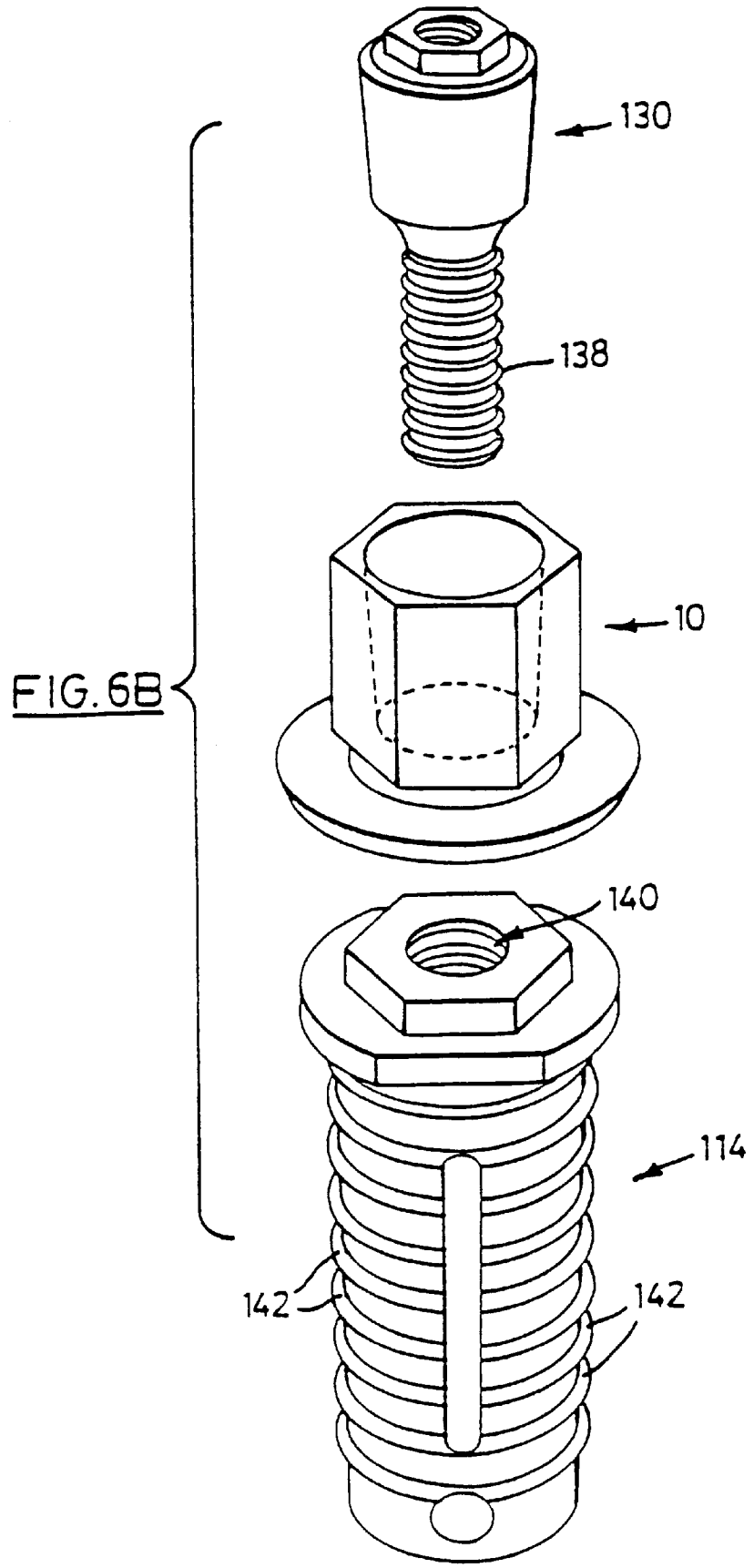

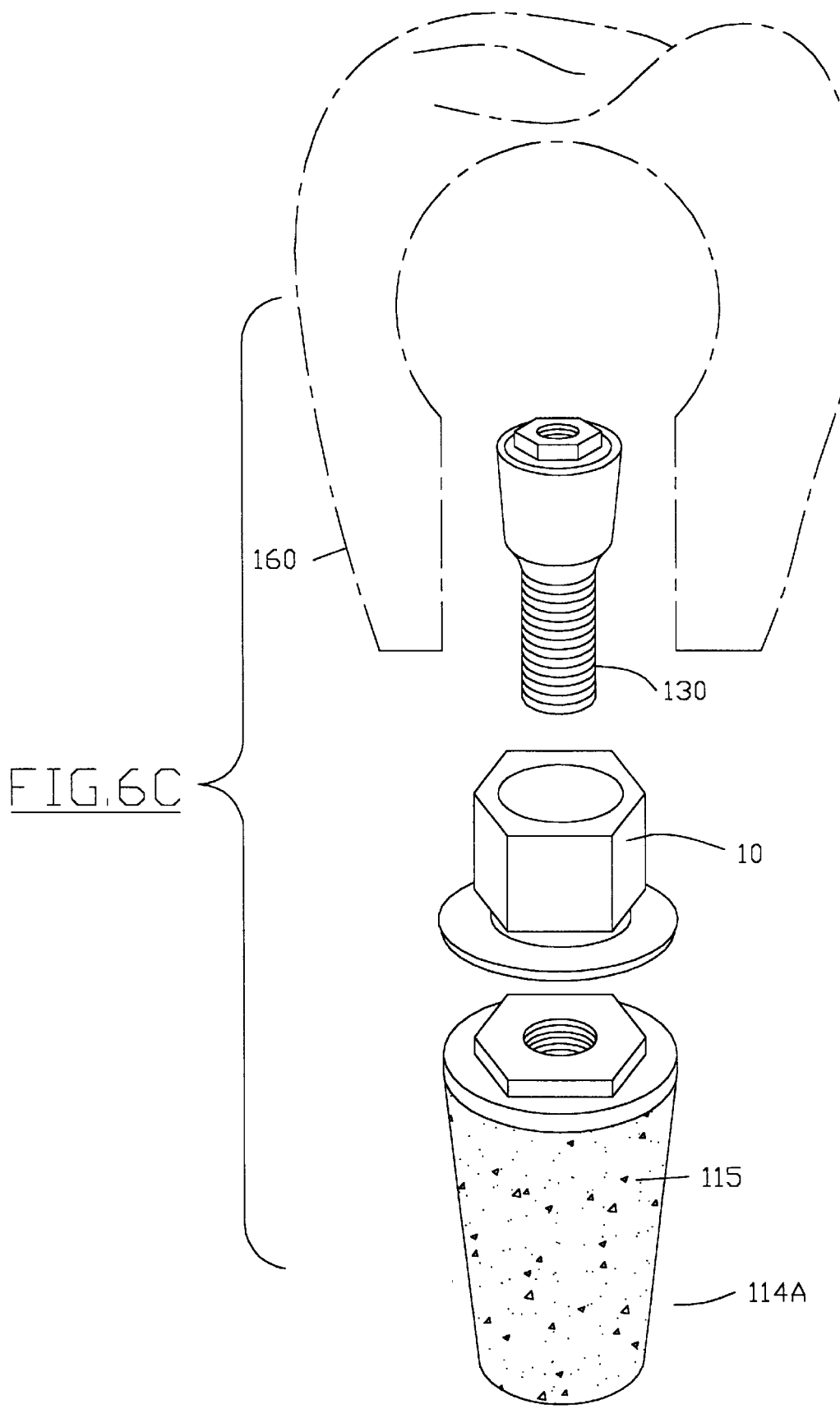

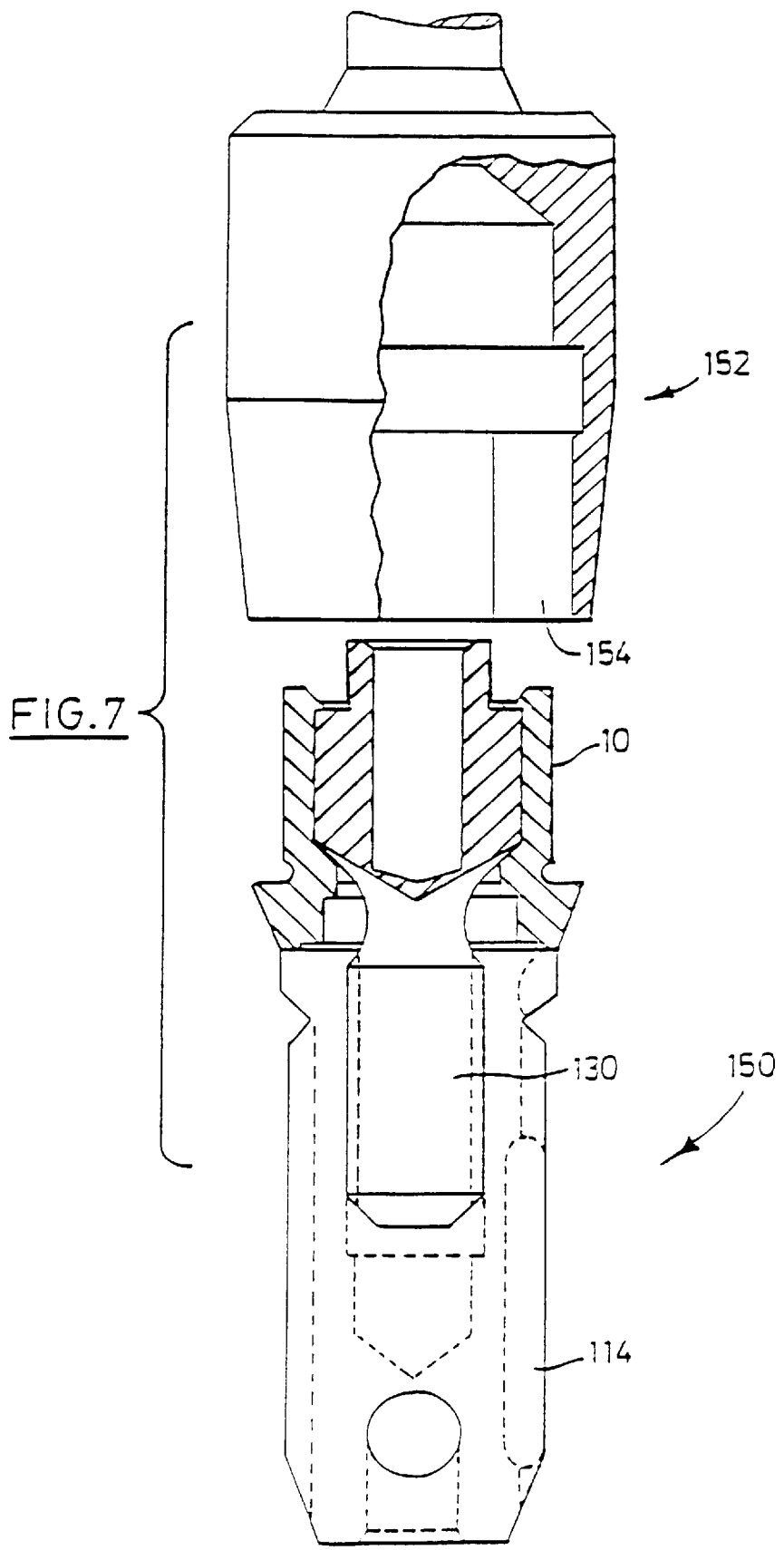

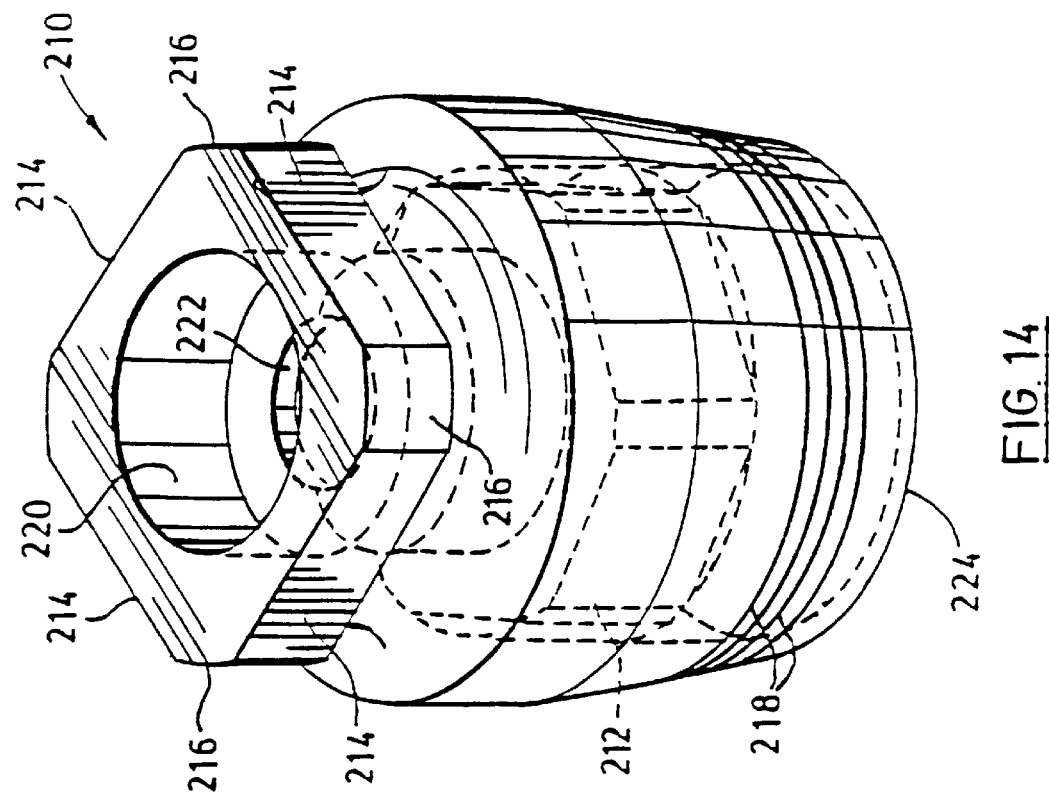
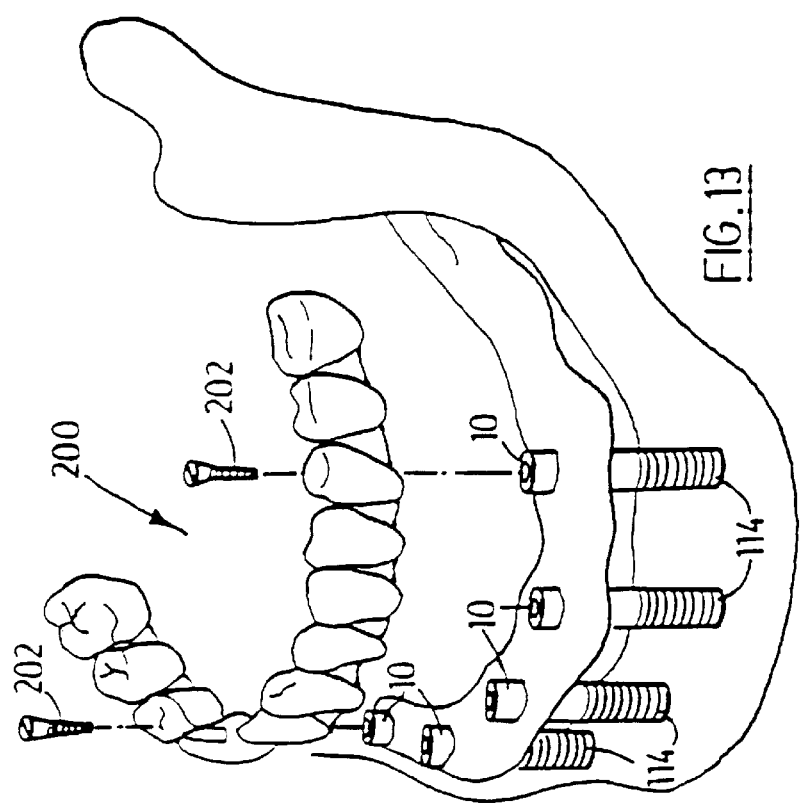
FIG. 14
FIG. 13

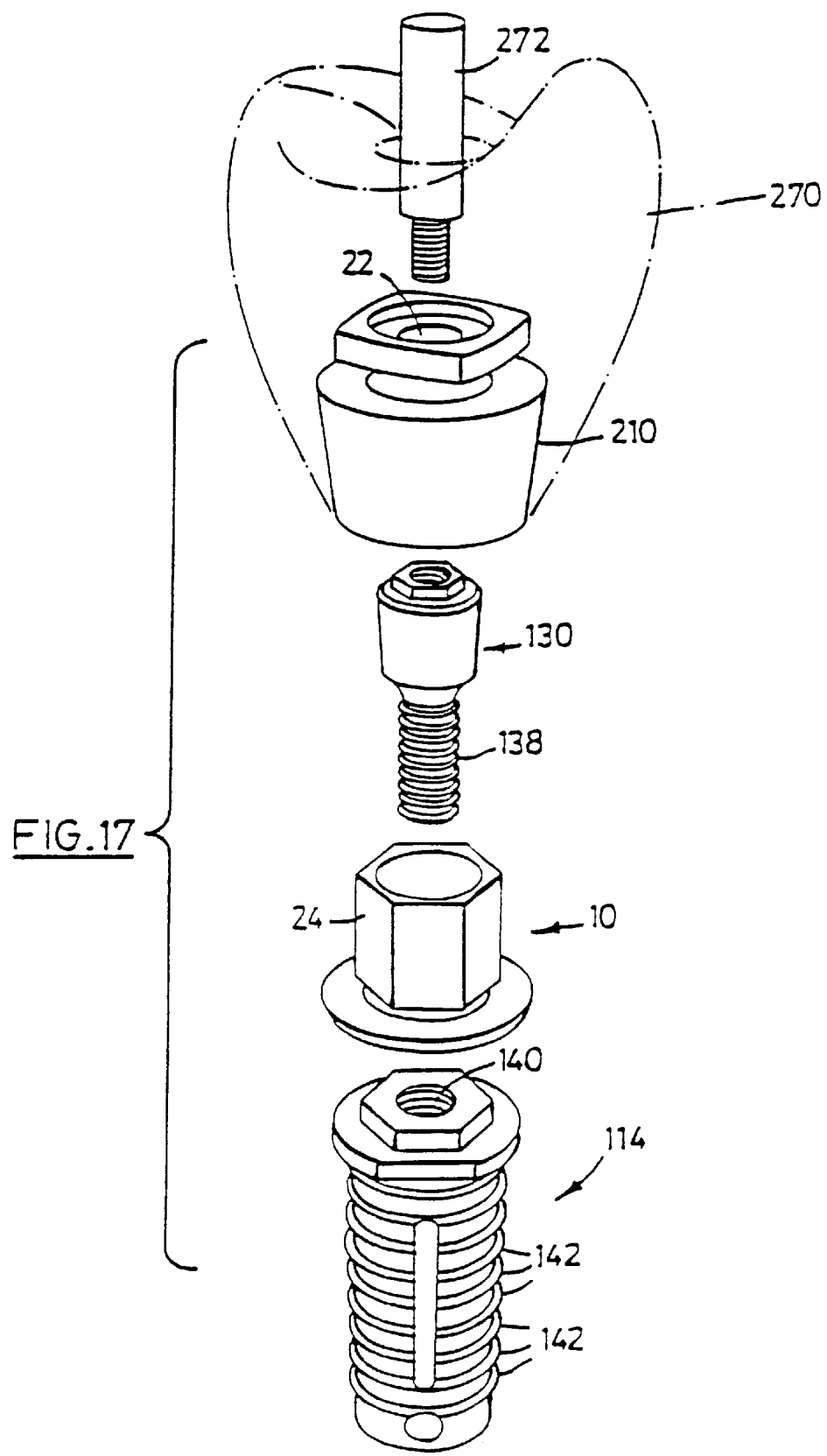

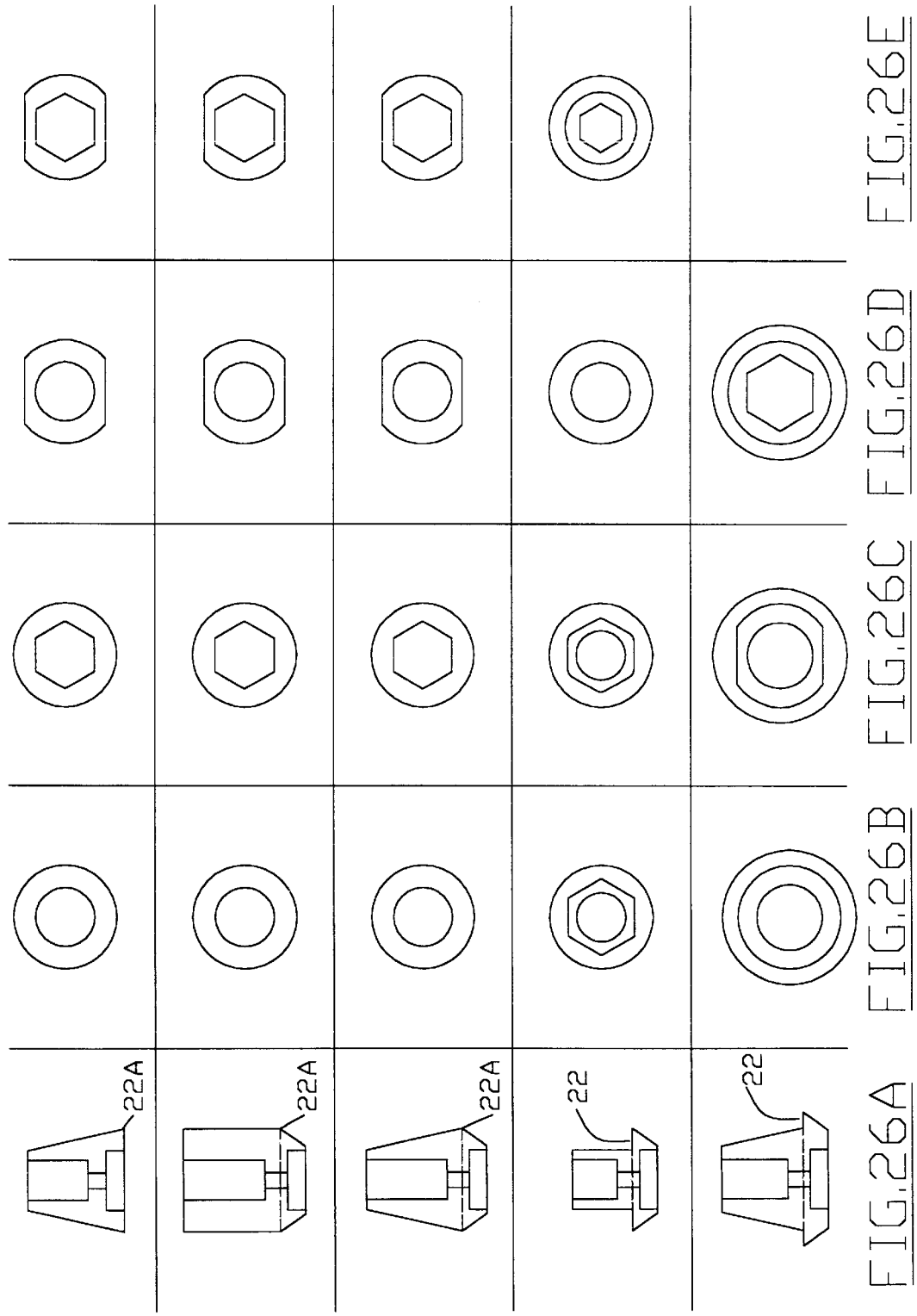

DENTAL IMPLANT SYSTEM

REFERENCE TO RELATED PATENT APPLICATIONS

This application is a continuation-in-part of applicant's patent application Ser. No. 08/654,315, filed on May 28, 1996, now U.S. Pat. No. 5,733,124 which in turn was a continuation-in-part of applicant's patent application Ser. No. 08/391,662, filed Feb. 21, 1995, now U.S. Pat. No. 5,564,924.

FIELD OF THE INVENTION

A dental implant system for securing an artificial tooth or dental prosthesis to the bone of a patient.

BACKGROUND OF THE INVENTION

Dental implants have been known, and used, since at least the 1930's; see, e.g., U.S. Pat. No. 5,312,254 of Joel L. Rosenlicht. See also U.S. Pat. No. 5,145,371 of Lars Jomeus which discusses the osseointegration method of integrating a dental implant into a patient's jaw. The disclosure of each of these patents is hereby incorporated by reference into this specification.

In applicant's U.S. Pat. No. 5,338,197, a dental implant having a cutting means is described and claimed; the disclosure of this patent is hereby incorporated by reference into this specification.

Another dental implant assembly is described in applicant's U.S. Pat. No. 5,564,924, which discloses a "HEXAGONAL ABUTMENT IMPLANT SYSTEM".

Dental implants are moderately expensive. It often costs from about three to four thousand dollars to implant a tooth into a patient's mouth.

One of the reasons for this substantial cost is the multiplicity of steps required by the implant procedure. These prior art steps will be described below with reference to Nobelpharma catalog PRI 385 94.03 2nd edition (published by the Nobelpharma AB, Box 5190, S-402 26 Goteborg, Sweden).

In the first step of the prior art procedure, an implant or "fixture" is purchased; see, e.g., page 7 of the Nobelpharma catalog and the reference to the 3.75 mm and 4.0 mm titanium fixtures illustrated on such page.

The fixture so purchased must then be placed into an "instrument set for fixture placement", which is shown on page 22 of the Nobelpharma catalog.

Once the fixture is disposed in the "instrument set . . . ", a "fixture mount" is then attached to the fixture by means of a wrench and a screwdriver. The "fixture mount" devices are shown on page 22 of the Nobelpharma catalog. The instruments for fixture placement of the fixture are also shown on page 22 of the Nobelpharna catalog (see wrench part 17 and screwdriver part 19).

Thereafter, a "connection to contra-angle handpiece" (see part 11 on page 22 of the Nobelpharma catalog) is attached to a handpiece (see page 31 of the Nobelpharma catalog); and the implant assembly may then be driven into the jawbone of a patient.

Thereafter, the fixture mount is removed from the fixture. Thereafter, a cover screw (see page 9 of the Nobelpharma catalog) is inserted into the fixture. Thereafter, the surgical site is allowed to heal for from about 3 to about 6 months. See, e.g., Branemark/Zarb/Alberektsson: "Tissue Integrated Prostheses" (Quintessence Books, 1985).

After the healing period, the implant is exposed by surgical procedures, and the cover screw is removed. Thereafter, a healing abutment (see page 39 of the Nobelpharma catalog) is attached to the fixture. It generally is left in place for from about two to about three weeks, depending upon how the patient's tissue has healed.

Thereafter, the healing abutment is then removed, and a implant abutment is then attached to the fixture. The type of implant abutment to be used will depend on the requirements of the patient. Thus, e.g., and referring to pages 38 and 39 of the Nobelpharama catalog, one may standard abutment, and "EsthetiCone" abutment, a "CeraOne" abutment, a "Ball Attachment", an Angulated Abutment", and the like.

Thereafter, the desired prosthesis is formulated by conventional means. Once the prosthesis has been prepared, it is fitted to the patient's mouth secured to the implant.

It will be apparent that this prior art procedure requires a myriad number of prosthetic instruments and parts, many trips by the patient to the dentist, and a several surgical procedures. Not only is the process tedious and expensive, but each surgical procedure introduces a certain element of risk, pain, and suffering.

It is an object of this invention to provide an implant assembly for implanting a prosthesis in a patient's mouth which is substantially less expensive, stronger, safer to use, and less-time consuming to use than the prior art implant assemblies.

It is another object of this invention to provide an implant assembly which, after it is secured to the patient, is less likely to become disengaged therefrom.

It is yet another object of this invention to provide an implant assembly which, after it is secured to the patient, provides substantially no opportunity for bacterial ingress within the assembly.

SUMMARY OF THE INVENTION

In accordance with this invention, there is provided a novel implant assembly comprised of an abutment integrally joined to a dental implant fixture and, optionally, a coping removably attached to the abutment. The abutment is preferably an integrally-formed, sleeve-shaped element containing a lower portion and an upper portion. The sleeve of the abutment preferably contains rounded corners which are compatible with the oral tissue and its functions in the patient's mouth.

BRIEF DESCRIPTION OF THE DRAWINGS

The present invention will be more fully understood by reference to the following detailed description thereof, when read in conjunction with the attached drawings, wherein like reference numerals refer to like elements, and wherein:

FIG. 2A is a sectional view of an abutment which is similar to the abutment of FIG. 2 but differs therefrom in omitting stepped bore 64;

FIG. 2C is a sectional view of an abutment which is similar to the abutment of FIG. 2 but differs therefrom in omitting three of its stepped bores 48, 63 and 64;

FIG. 6B is an exploded perspective view illustrating how the retaining screw of FIG. 6A may be attached to an abutment and an implant fixture.

FIG. 6C is an exploded view of one preferred assembly of this invention;

FIG. 7 is an exploded view an abutment implant assembly being driven into bone;

FIG. 11 is a sectional view of a the abutment/implant system being connected to a standard gold cylinder.

FIG. 14 is a perspective view of a gold coping device which may be used with applicant's abutment system;

FIG. 17 is a an exploded perspective view illustrating how the gold coping device may be attached within a tooth and secured to the abutment;

FIGS. 26A, 26B, 26C, 26D, and 26E are sectional views which schematically illustrate the various combinations of the outer shapes of the base, the inner shapes of the base's orifices, and the shapes of the abutment which may be used in the assembly of the invention;

FIGS. 26A and 26B are partial perspective views illustrating other preferred assemblies of the invention.

DESCRIPTION OF THE PREFERRED EMBODIMENTS

Figure 1:
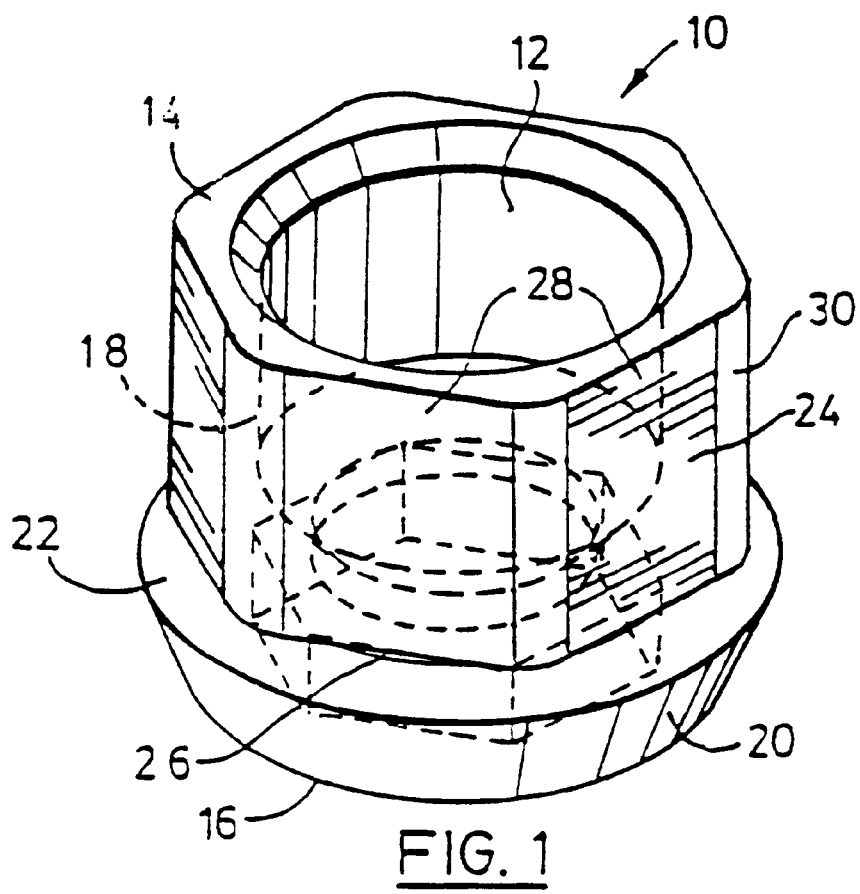
FIG. 1 is a perspective view of one preferred abutment of this invention.

Referring to FIG. 1, a perspective view of one preferred abutment 10 is shown. This abutment 10 is preferably an integral structure which consists or consists essentially of titanium or titanium alloy. Alternatively, the abutment 10 may consist of gold, silver, palladium, vanadium, cobalt alloy, stainless steel, and the like. Alternatively, the abutment 10 may consist or consist essentially of a castable plastic material such as, e.g., acrylic polymeric material.

In one preferred embodiment, abutment 10 consists or consists essentially of alumina. Alternatively, or additionally, the abutment 10 may consist or consist essentially of one or more other ceramic materials.

By way of illustration and not limitation, any of the titanium or titanium alloy materials used in implants may be used to make abutment 10. Thus, e.g., one may use one or more of the materials disclosed in U.S. Pat. No. 5,373,621 (a titanium/aluminum/vanadium alloy), U.S. Pat. No. 5,372,660 (a titanium/zirconium alloy), U.S. Pat. No. 5,358,529, U.S. Pat. No. 5,354,390 (a titanium-base microalloy containing at least 98 weight percent of titanium), U.S. Pat. No. 5,334,264 (a nitrided titanium material), U.S. Pat. No. 5,326,362 (a titanium/aluminum/vanadium alloy), U.S. Pat.

No. 5,205,921 (a coated titanium implant), U.S. Pat. No. 5,192,323 (a titanium/aluminum/vanadium alloy), and the like. The disclosure of each of these United States patents is hereby incorporated by reference into this specification.

In one preferred embodiment, abutment 10 is machined from pure titanium which, preferably, is originally in the form of a rod. It is preferred that the titanium used meet the standards set forth in A.S.T.M. Standard F 67-88, "Specification for Unalloyed Titanium for Surgical Implant Applications." In general, it is also preferred that the material used, regardless of whether it is titanium, titanium alloy, and/or other material, meet the requirements set forth in A.S.T.M. Standard Test F 981-87 "Practice for Assessment of Compatibility of Bio Materials (Non-Porous) for Surgical Implants".

Figure 2:
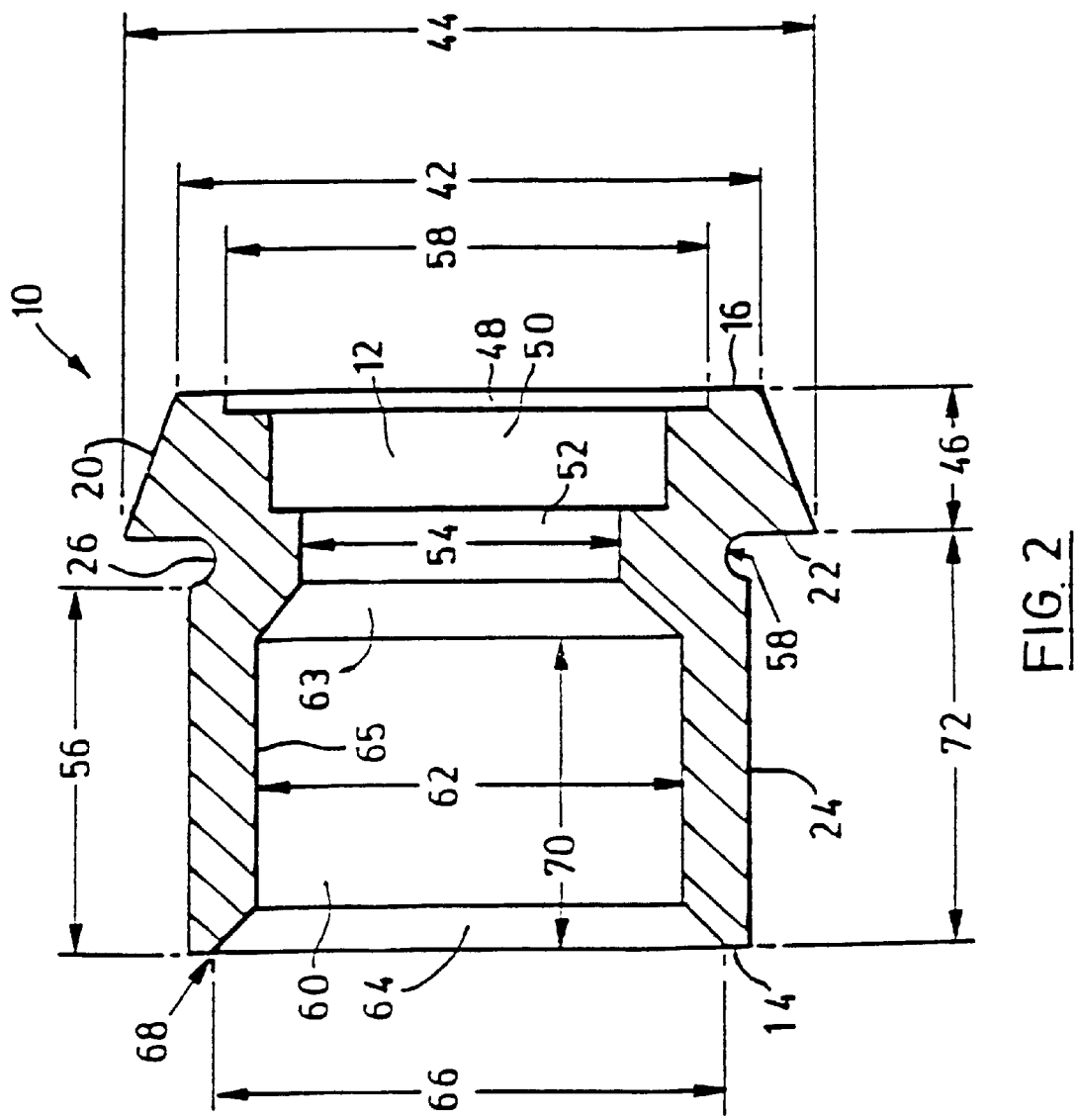
FIG. 2 is a sectional view of the abutment of FIG. 1.

Referring again to FIG. 1, it will be seen that abutment 10 is comprised of a hollow core 12 which extends from the top 14 of abutment 10 to its bottom (not shown in FIG. 1, but see bottom 16 in FIG. 2). The hollow core 12 is indicated in FIG. 1 by dotted line 18.

Referring again to FIG. 1, and in the preferred embodiment depicted therein, it will be seen that abutment 10 is comprised of a base 20 which extends upwardly and outwardly from its bottom 16 to form an intermediate ledge 22. Other configurations of abutment 10 are described elsewhere in this specification.

The term ledge, as used in this specification, refers to a outwardly extending projection forming a shelf. In the embodiment depicted in FIG. 1, the ledge 22 extends substantially horizontally. In the embodiment depicted in, e.g., FIG. 24B, the ledge 22A is formed at the intersection of walls 22B and 22C. As will be apparent to those skilled in the art, the ledge of the assembly provides a means for mating with a dental prosthesis which is inserted over the top portion of the abutment.

FIG. 2 better illustrates the preferred structure near ledge 22 of FIG. 1. It will be seen that, in the preferred embodiment illustrated, ledge 22 is disposed beneath substantially hexagonal portion 24 of abutment 10. Disposed between substantially hexagonal portion 24 and ledge 22 is annular groove. Without wishing to be bound to any particular theory, applicant believes that this structure provides a more secure attachment to devices attachable to abutment 10.

As will be apparent to those skilled in the art, other configurations which provide the same function as ledge 22 are also ledges within the meaning of the claims of this case.

Figure 1A:
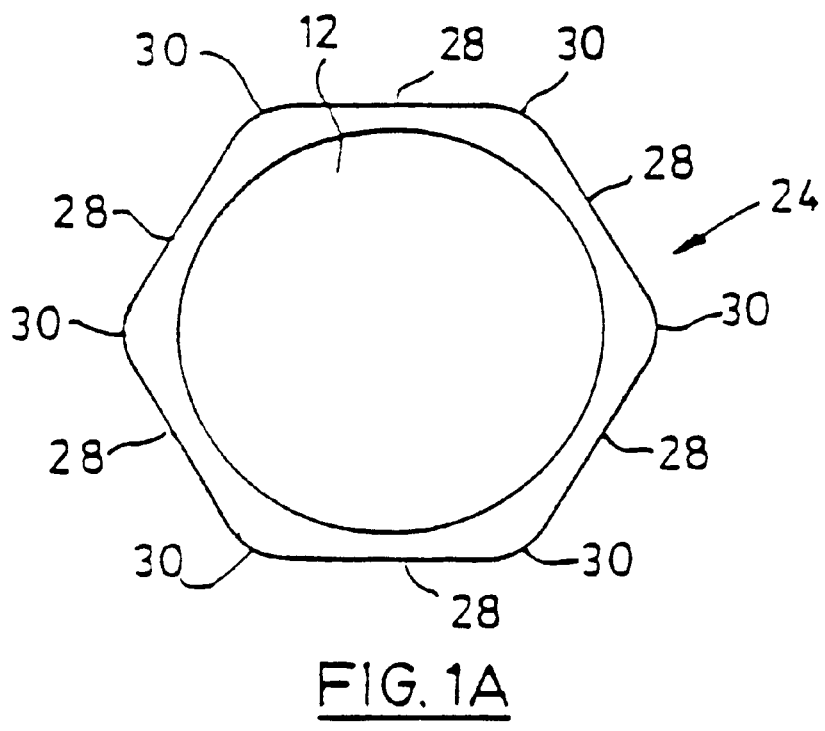
FIG. 1A is a top view of an abutment with a substantially hexagonal exterior shape.

Referring again to FIG. 1, and in the preferred embodiment depicted therein, it seen that the substantially hexagonal portion preferably has rounded corners. This is also illustrated in FIG. 1A, which is a partial top view of the structure of FIG. 1.

As will be apparent to those skilled in the art, and as is specifically illustrated elsewhere in this specification, other configurations with alternating linear and arcuate sections also may be used.

Referring again to FIG. 1A, it will be seen that hexagonal portion 24 is comprised of an exterior surface which contains alternating linear portions 28 and arcuate portions 30. Without wishing to be bound to any particular theory, it is believed that the rounded corners (arcuate portions 30) in this structure are substantially compatible with the patient's mouth. Thus, e.g., these rounded corners do not irritate the patient's tongue during eating as much as the sharp corners present on normal hexagonal structures.

In one embodiment, not shown in FIG. 1, the hexagonal portion 24 contains only or primarily linear portions 28. In this embodiment, a healing ball (not shown in FIG. 1) may be placed over hexagonal portion 24 to prevent contact therewith with the patient's mouth. The healing ball may have different cross-sectional shapes such as, e.g., circular, the anatomic shape of a tooth, an irregular shape, etc.

In the preferred embodiment depicted in FIG. 1, it is preferred that the length of each linear portion 28 be substantially equal to the length of each of the other linear portions 28. In one embodiment, the substantially hexagonal shape depicted in FIG. 1 is substantially symmetrical.

In this preferred embodiment, it is also preferred that the length of each linear portion 28 be at least about 1.2 times as long as the length of each curved portion 30. In one preferred embodiment, the length of each linear portion 28 is at least about 3.0 times as great as the length of each curved portion 30.

Figure 1B:
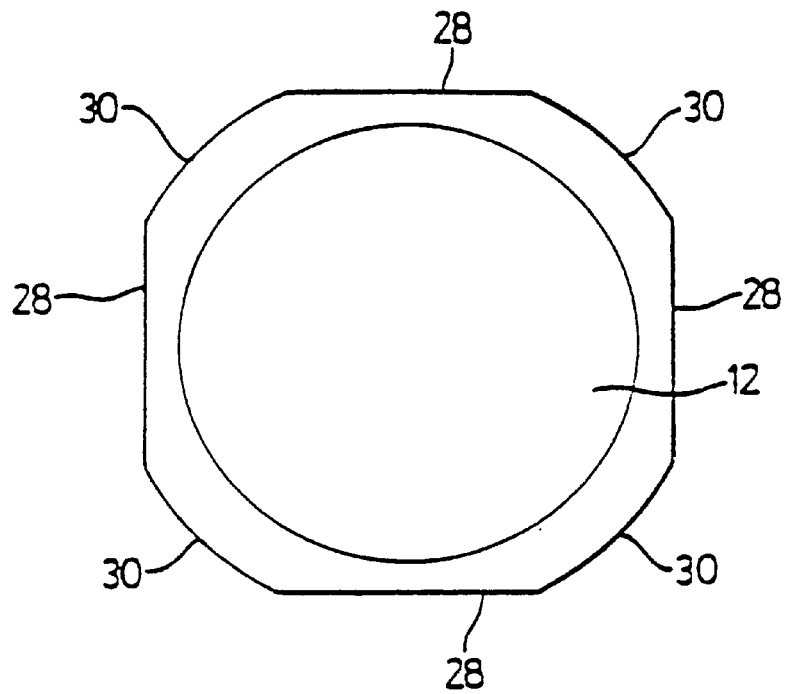
FIG. 1B is a top view of an abutment with a substantially square exterior shape.
Figure 1C:
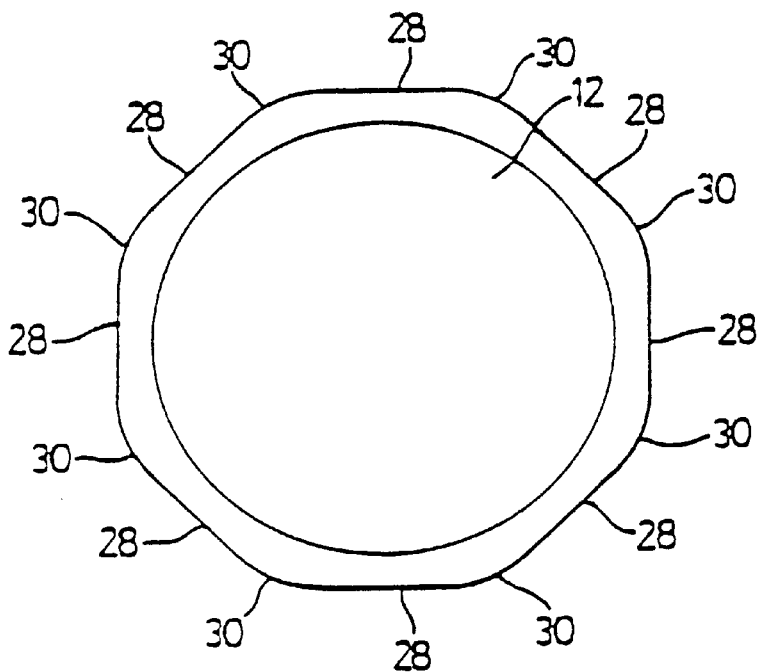
FIG. 1C is a top view of an abutment with a substantially octagonal exterior shape.

As will be apparent to those skilled in the art, the abutment 10 may have an exterior shape which need not be substantially hexagonal but may assume the shape of other polygons. Thus, FIG. 1B depicts a substantially square cross-sectional shape. Thus, FIG. 1C depicts a substantially octagonal cross-sectional shape.

As will be apparent to those skilled in the art, substantially any polygonal shape can be used which is capable of being mechanically engaged. Thus, by way of further illustration, one may use substantially triangular shapes, substantially rectangular shapes, substantially pentagonal shapes, substantially heptagonal shapes, substantially nonagonal shapes, and the like. What is required in this embodiment of any such shape, however, is that it contain alternating linear and non-linear sections (the latter preferably being arcuate) and that, preferably, they define a shape which is symmetrical along at least one axis of symmetry.

FIG. 2 is a sectional view of the abutment 10 of FIG. 1. Referring to FIG. 2, and in the preferred embodiment depicted therein, it will be seen that the base 20 of abutment 10 preferably has a width 42 at its bottom which is substantially less than its width 44 at its top. In general, width 44 is at least about 1.1 times as great as width 42. In one preferred, with 44 is 4.7 millimeters, and width 42 is 4.0 millimeters.

Referring again to FIG. 2, it will be seen that base 20 has a depth 46 which, preferably, is from about 0.5 to about 7.0 millimeters and, more preferably, is from about 0.5 to about 1.5 millimeters. In the preferred embodiment illustrated in FIG. 2, depth 46 is 1.0 millimeter.

Referring again to FIG. 2, and in the preferred embodiment depicted therein, it will be seen that, near base 20, hollow core 12 is comprised of stepped bores 48, 50, and 52.

Stepped bore 52 has a diameter 54 sufficient for a screw (not shown) to pass through it. In the preferred embodiment illustrated in FIG. 2, stepped bore 52 has a diameter 54 of 2.2 millimeters.

Figure 2B:
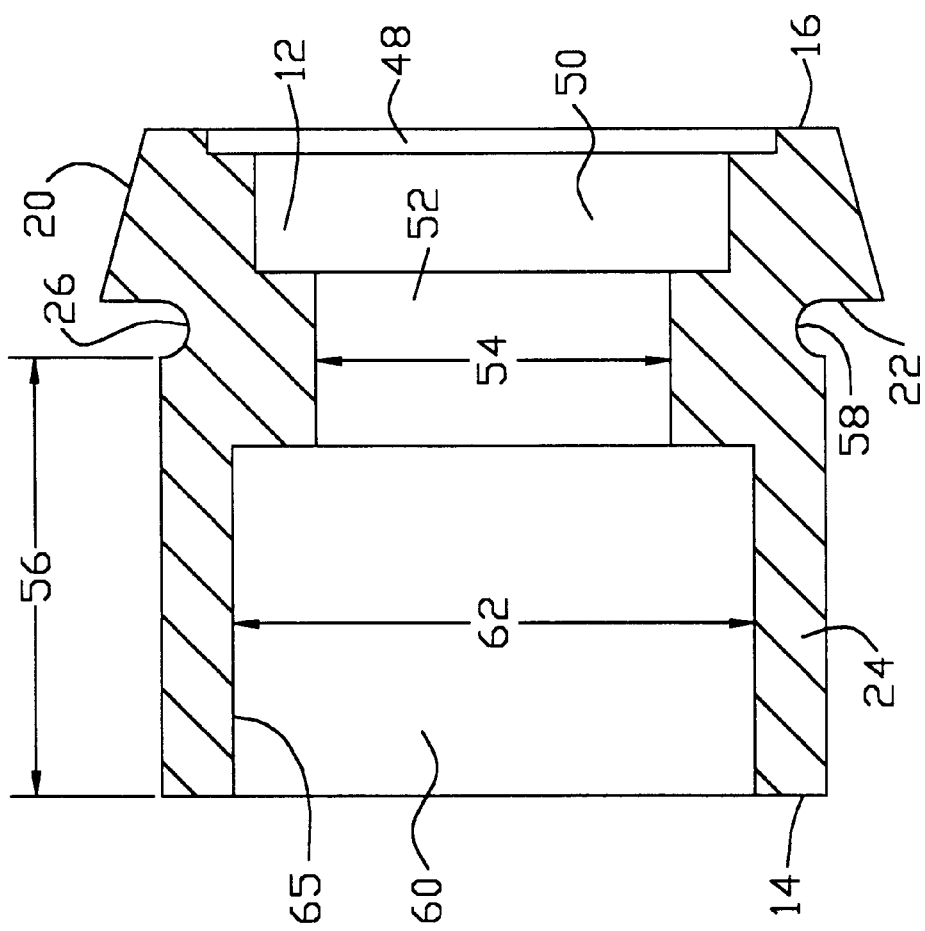
FIG. 2B is a sectional view of an abutment which is similar to the abutment of FIG. 2 but differs therefrom in omitting two of its stepped bores, bores 63 and 64.

In the embodiments depicted in FIGS. 2A, 2B, and 2C one or more of stepped bores 48, 62, and 63 have been eliminated.

Referring again to FIG. 2, and in the preferred embodiment depicted therein, it will be seen that substantially hexagonal portion 24 extends from the top 14 of abutment 10 to annular groove 26. It is preferred that the distance 56 between top 14 and annular groove 26 of abutment 10 extend at least about 55 percent of the entire height of abutment 10. In one preferred embodiment, distance 56 is about 3.0 millimeters.

It is preferred that annular groove 26 have a substantially circular shape and, more preferably, have a radius of curvature 58 of from about 0.1 to about 0.2 millimeters. In one preferred embodiment, the radius of curvature of groove 26 is about 0.15 millimeters.

Referring again to FIG. 1, and in the preferred embodiment depicted therein, bore 48 has a diameter 58 of about 3.5 millimeters, bore 60 has a diameter 62 of about 3.0 millimeters, bore 64 has a diameter 66 at its top most point of about 3.5 millimeters, the distance 70 between point 68 and the end of bore 60 is 2.0 millimeters, and the distance between surface 68 and ledge 22 is 3.0 millimeters.

Figure 3:
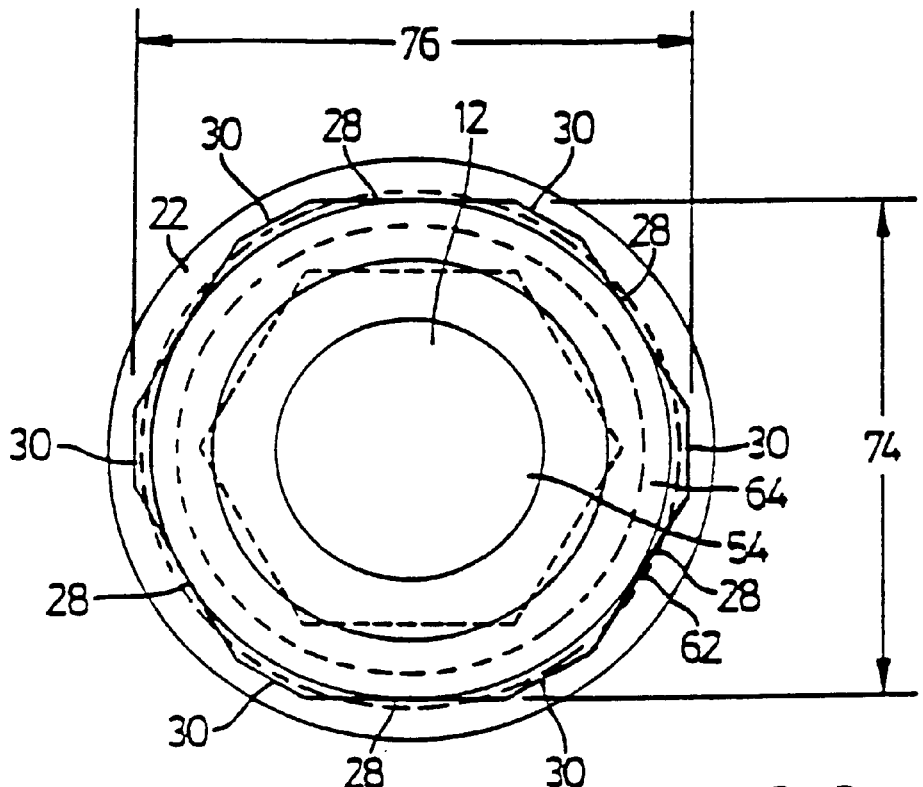
FIG. 3 is a top view of the abutment of FIG. 1.

FIG. 3 is a top view of abutment 10. In the preferred embodiment depicted in FIG. 3, the distance 74 between opposite linear surfaces on the exterior of the hexagonal sleeve preferably is about 3.9 millimeters; and the distance 76 between opposite arcuate surfaces on the exterior of the hexagonal sleeve is about 4.1 millimeters.

Figure 4:
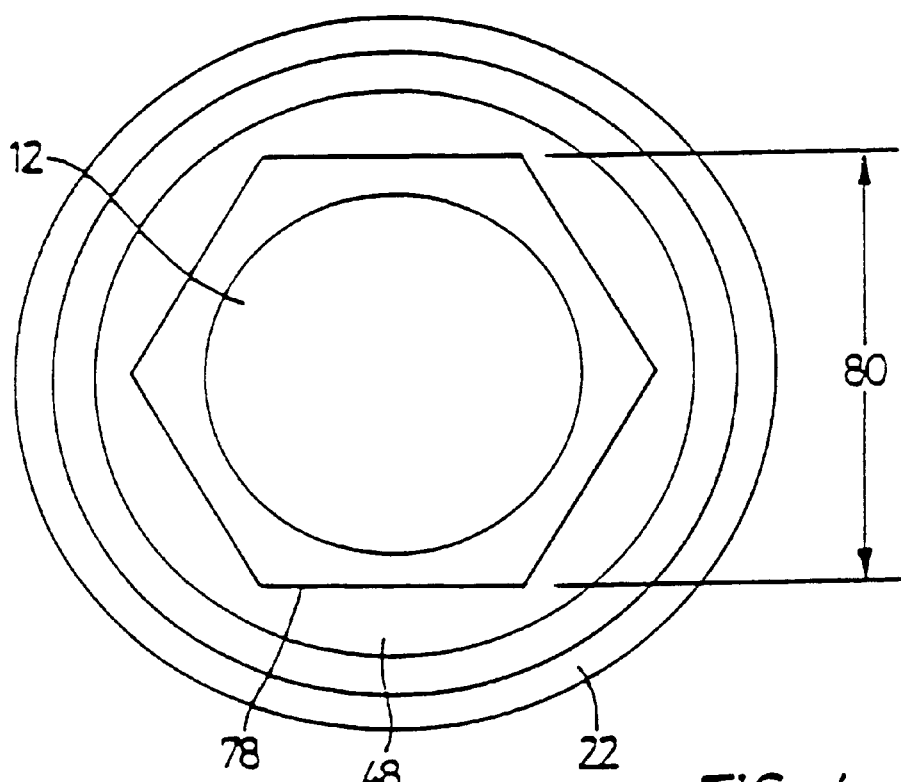
FIG. 4 is a bottom view of the abutment of FIG. 1.

FIG. 4 is a bottom view of abutment 10. Referring to FIG. 4, and in the preferred embodiment depicted therein, it will be seen that bore preferably has a substantially hexagonal cross-sectional shape 78 which is adapted to mate with the external hexagonal shape of the upper portion of an implant fixture (not shown); in other embodiments discussed elsewhere in this specification bores with other shapes are discussed. In the preferred embodiment shown, the distance 80 between opposing linear walls of said hexagonal shape is preferably 2.7 millimeters.

Referring again to FIG. 2, and in the preferred embodiment depicted therein, it will be seen that bore 63 is disposed between bore 60 and bore 52 and has a diameter which continually decreases from bore 60 to bore 52, thereby forming a chamfered surface. It is preferred that said chamfered surface form an obtuse angle (as measured with respect to the interior wall 65 of bore 60) of from about 120 to about 150 degrees.

Figure 5:
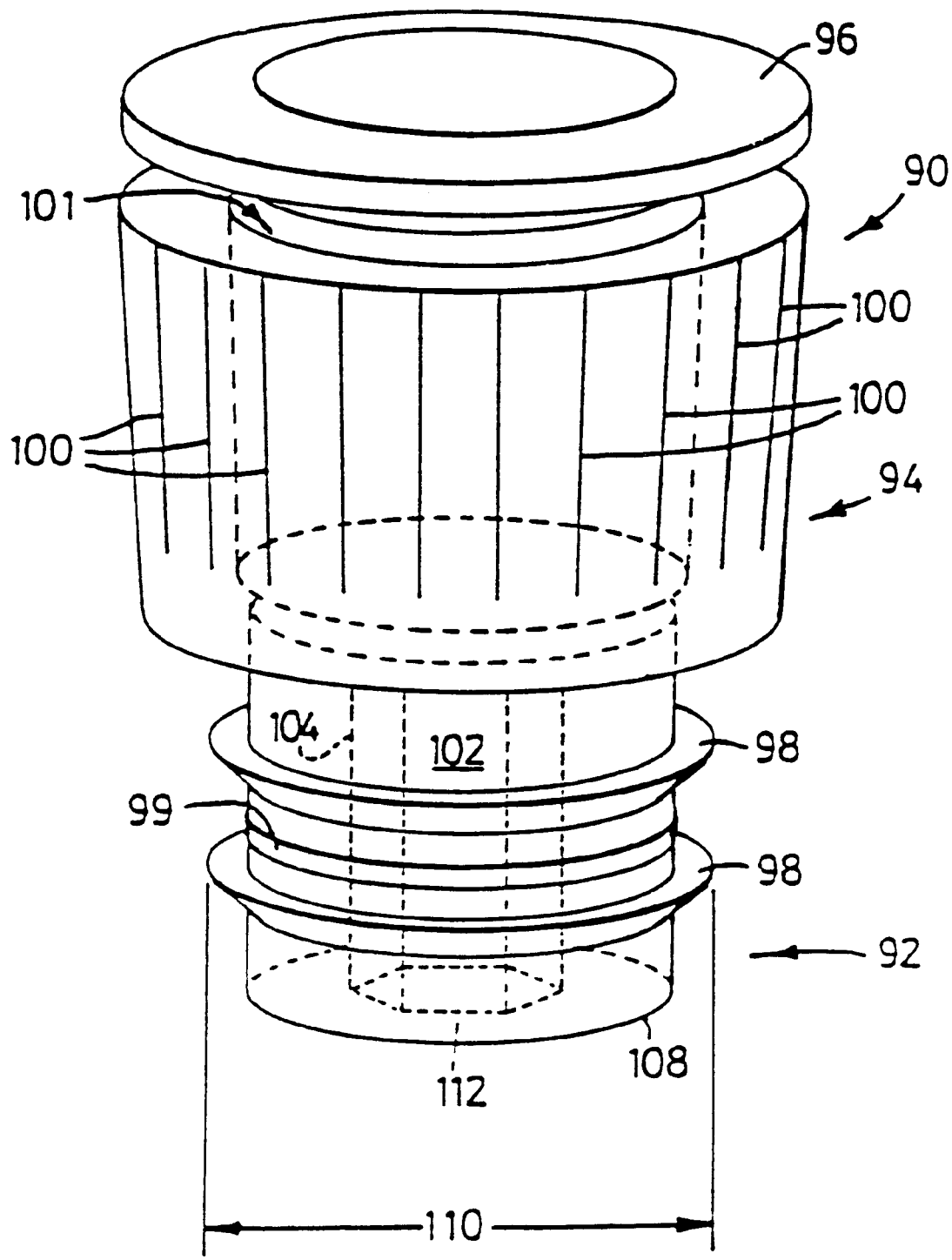
FIG. 5 is a perspective view of a carrier adapted to be used with the abutment of FIG. 1.

FIG. 5 is a perspective view of carrier 90 which is adapted to be removably connected to abutment 10 and to manually deliver it into the jaw of a patient.

Referring to FIG. 5, it will be seen that carrier 90 is preferably an integral assembly which, preferably, consists essentially of plastic material which, preferably, is non-toxic and thus is "medical grade."

One may use any of the "medical grade" materials known to those skilled in the art such as, e.g., the plastics described in U.S. Pat. No. 5,356,709 (polypropylene copolymyer; styrene/ethylene/butylene/styrene copolymer), U.S. Pat. No. 5,312,251 (medical grade ceramic material), U.S. Pat. No. 5,326,364 (medical grade ceramic), and the like. The disclosure of each of these United States patents is hereby incorporated by reference into this specification.

In one preferred embodiment, carrier 90 consists essentially of high density polypropylene which is extruded into the desired shape.

Referring again to FIG. 5, it will be seen that carrier 90 is comprised of a fin 92, grip 94, and removable cover 96. The fin 92 is comprised of external annular ridges 98 which are adapted to fit within and be contiguous with a shipping vial(not show in FIG. 5). The grip 94 is preferably comprised of a multiplicity of vertically-extending ridges 100 which facilitate the handling of grip 94; and will be apparent to those skilled in the art, other means of facilitating the handling of grip 94 (such as, e.g., roughened surfaces) may also be used.

Within grip 94 is a compartment 101 in which an accessory part (not shown) may be stored. Removable cover 96 is adapted to snap into place within such compartment 101.

In one embodiment, removable cover 96 is color coded to indicate which part it is to be used in connection with.

A bore 102 (shown in outline by dotted line 104) extends from the top 106 of fin 92 to the bottom 108 of fin 92. That portion of bore 102 extending through fin 92 has a substantially hexagonal cross-sectional shape and, thus, is adapted to fit over and engage with the substantially hexagonal portion 24 of abutment 10.

In one preferred embodiment, illustrated in FIG. 5, the width 110 of fin 92 is about 9.9 millimeters, and maximum dimensional of the hexagonally shaped bore 102 as it exits fin 92 is about 4 millimeters.

In the preferred embodiment illustrated FIG. 5, the bottom surface 112 of the carrier 90 is preferably a flat surface adapted to mesh with the flat surface of ledge 22 (see FIGS. 1, 2, and 6) so that the carrier 90 is properly aligned with abutment 10 when it is removably connected thereto.

Figure 6:
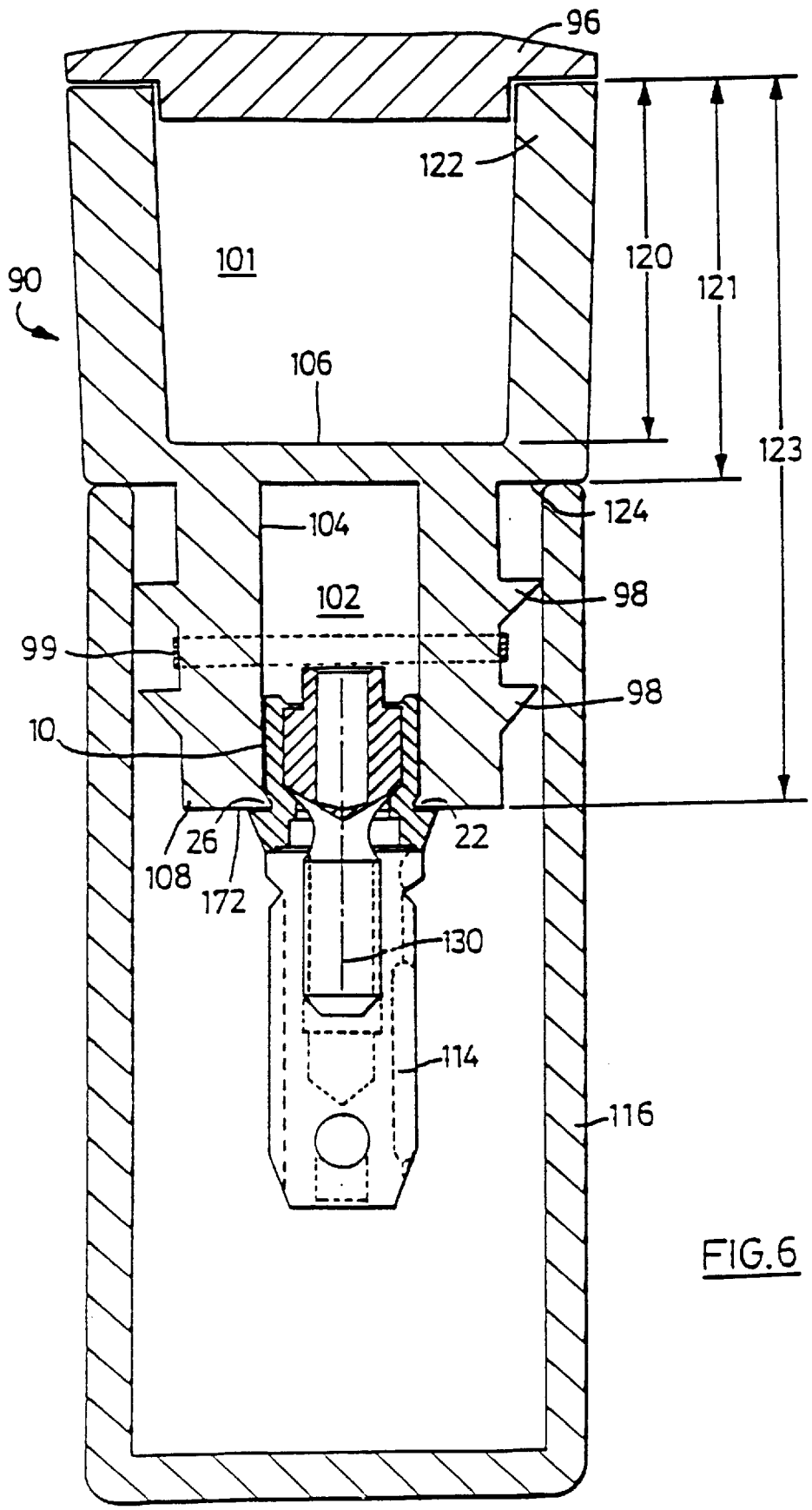
FIG. 6 is a sectional view of the carrier of FIG. 5 connected to the abutment of FIG. 1, which in turn is connected to an implant fixture, the whole assembly being disposed within a vial.

FIG. 6 is a sectional view of carrier 90 connected to abutment 10 which, in turn, is connected to implant fixture 114, the abutment and implant being disposed within a vial 116.

Referring to FIG. 6, and in the preferred embodiment illustrated therein, it will be seen that carrier 90 is removable connected to both cover 96, vial 116, and abutment 10, all by a friction fit. The entire assembly may be disposed in another vial (not shown). In this embodiment, the depth 120 of compartment 101 is preferably from about 5 to about 10 millimeters, the distance 121 between the top lip 122 and the bottom surface 124 of the grip 90 is from about 6 to about 12 millimeters, and the distance 123 from the top of carrier 90 to its bottom is from about 10 to 20 millimeters.

Referring again to FIG. 6, it will be seen that the carrier 90/abutment 10/vial 16 assembly may be used in conjunction with an implant fixture 114. This assembly is quite adaptable and may be used with substantially any of the implant fixtures known to those skilled in the art.

Thus, by way of illustration and not limitation, one may use one or more of the implant fixtures disclosed in U.S. Pat. Nos. 5,338,197, 5,061,181, 5,030,095, 4,960,381, 4,932, 868, 4,871,313, 4,854,873, 4,854,872, 4,713,004, 4,468,200, 4,330,891, 4,016,651, 3,672,058, 3,579,831, 2,609,605, 5,376,004, 5,364,268, 5,362,235, 5,302,125, 5,628,630, and the like. The disclosure of each of these United States patents is hereby incorporated by reference into this specification.

In one preferred embodiment, the dental implant is coated with a pure metal porous coating formed by the thermal decomposition of a coating of thermally-decomposable metal compound particles and sintering of the metal particles. Such a coating is disclosed in U.S. Pat. No. 4,206,516 of Pilliar, the entire disclosure of which is hereby incorporated by reference into this specification. Such a dental implant is illustrated in FIG. 6C (see element 114A).

As will be apparent to those skilled the art, many different coatings can be used on the surface 115 of element 114A. Thus, by way of illustration, one may use the porous beaded surface illustrated, one may use hydroxyapatite, one may use a coating formed by titanium plasma spray, and one may use other materials adapted to promote the healing of human bones.

By way of further illustration, and referring to the Nobelpharma catalog referred to elsewhere in this specification, one may use any of the implant fixtures disclosed on page 7 of such catalog.

Referring again to FIG. 6, it will be seen that implant fixture 114 is preferably connected to abutment 10 by means of retaining screw 130. The retaining screw 130 is shown in more detail in FIG. 6A.

Figure 6A:
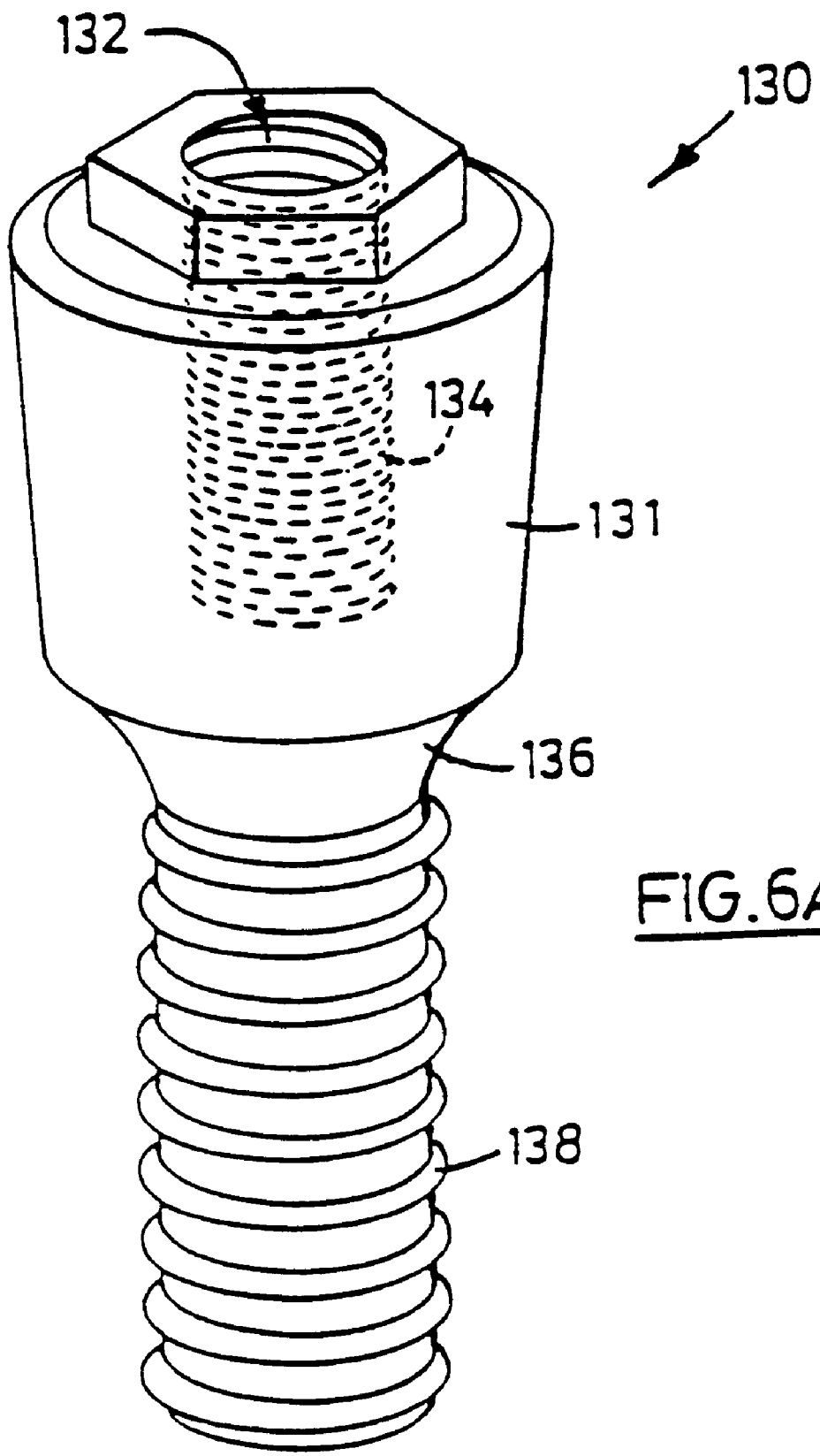
FIG. 6A is a perspective view of an abutment retaining screw which can be used with the abutment of this invention.

Referring to FIG. 6A, it will be seen that retaining screw 130 is comprised of an internal bore 132 with internal threads 134 adapted to receive and engage with the external threads on a multiplicity of dental prostheses (not shown).

In the preferred embodiment illustrated, the retaining screw 130 is comprised of tapered section 136 which is adapted to fit within bore 63 (see FIG. 2) and mesh with the tapered section therein. Other suitable retaining screw configurations will be apparent to those skilled in the art.

The retaining screw 130 is also comprised of external threads which, after they pass through abutment 10, may be secured to internal threads (not shown) in the implant fixture (not shown in FIG. 6A).

FIG. 6B is an exploded perspective view illustrating that, after retaining screw 130 is passed through abutment 10, it may be screwed into orifice 140 of implant fixture 114 and become screwably engaged with the internal threads located within orifice 140.

In the preferred embodiment illustrated in FIG. 6B, implant fixture 114 is comprised of external threads 142 which can be used to secure implant assembly within the jawbone of a patient.

FIG. 7 is an exploded view showing the abutment 10/retaining screw 130/implant fixture 114 assembly 150 disposed beneath a socket wrench 152 with a hexagonal bore 154. As will be apparent to those skilled in the art, socket wrench 152 may be removably attached to the substantially hexagonal portion 24 of abutment 10 and used to insert assembly 150 into a hole in the patient's jaw. Alternatively, or additionally, depending upon the amount of force needed, carrier 90 may be used for this purpose or, alternatively, to start the insertion of the assembly 150 in said hole.

In the embodiment illustrated in FIG. 7, the implant fixture has an exterior hexagonal shape; and thus it is adapted to be screwed into the hole in the patient's jaw by a socket wrench with a matching hexagonal bore. It will be apparent, however, that the means of inserting the assembly 150 into the hole in the patient's jaw will vary with the type of implant 114 used. Thus, for example, when the exterior shape of implant 114 is substantially cylindrical, a seating tool (such as a mallet) may be used. These procedures are well known to those skilled in the art.

Figure 8:
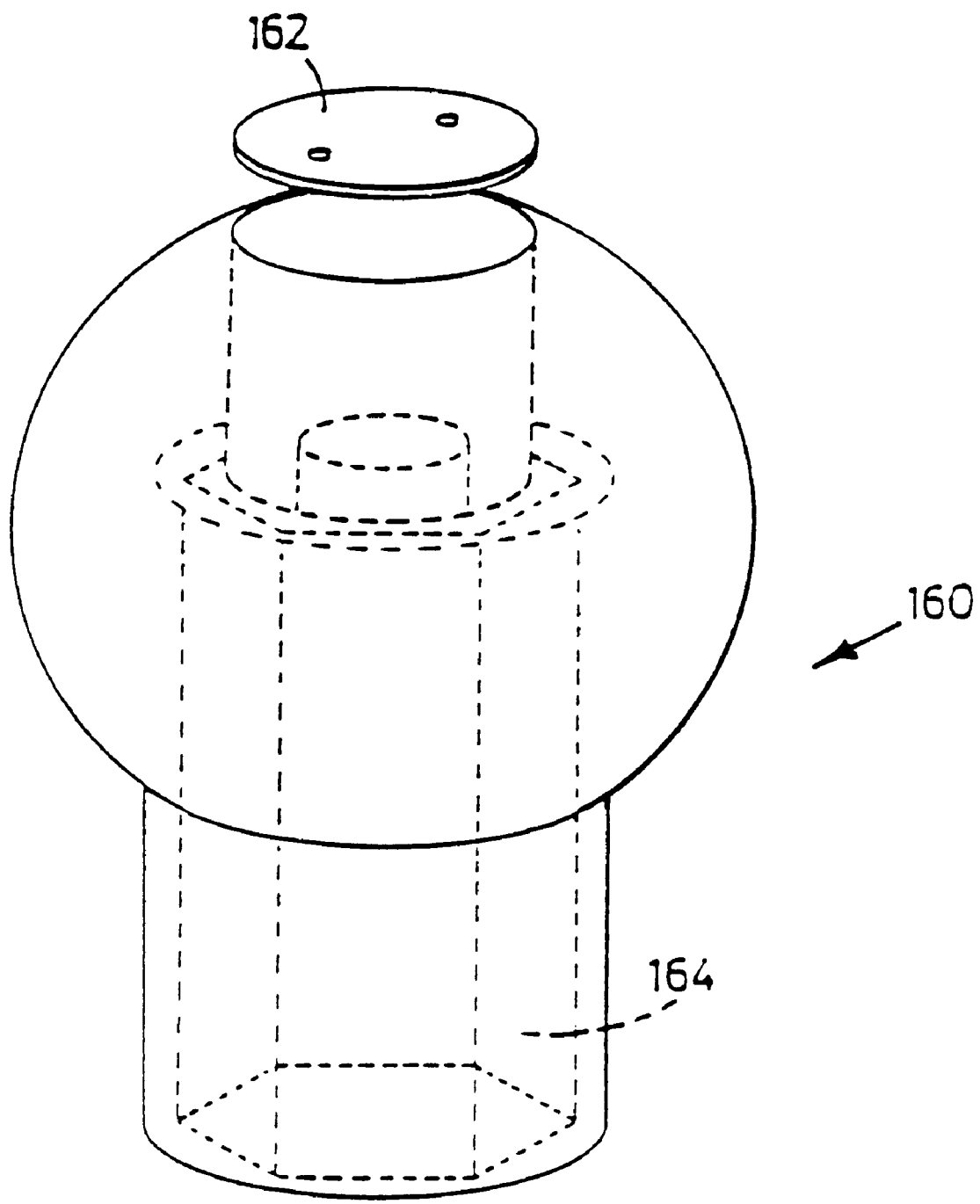
FIG. 8 is view of a healing abutment which is adapted to fit over the hexagonal abutment of FIG. 1.

FIG. 8 is a perspective view of a healing ball 160 which may be used in connection with abutment 10. Referring to FIG. 8, it will be seen that healing ball 160 is comprised of a removable cover 162.

Healing ball 160 preferably consists essentially of medical grade material such as, e.g., medical grade polyethylene. In one preferred embodiment, healing ball 160 consists essentially of high density polyethylene.

Figure 9:
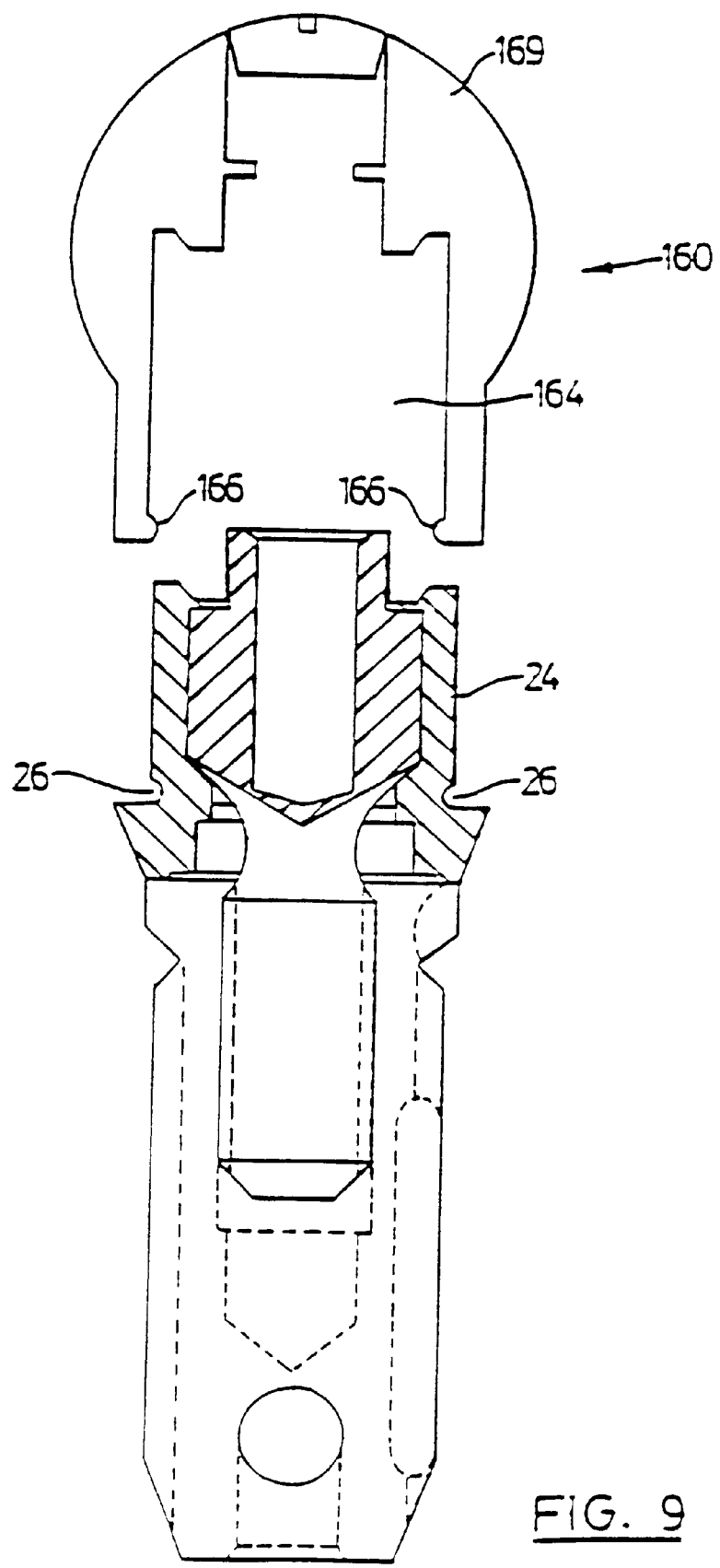
FIG. 9 is a sectional view of the healing abutment connected to applicant's abutment/implant system.

Referring again to FIG. 8, and in the preferred embodiment depicted therein, it will be seen that healing ball 160 is comprised of an internal bore 164 which has a substantially hexagonal shape and is adapted to fit snugly over the substantially hexagonal portion 24 of abutment 10 (see FIG. 9).

The healing ball depicted in FIG. 8 is but one of many such dental copings which may be used in the assembly of this invention. Thus, by way of illustration and not limitation, one may use one or more of the dental copings described in U.S. Pat. Nos. 5,613,854, 5,571,016, 5,476,383 (transfer coping), U.S. Pat. Nos. 5,439,380, 5,419,702 (companion transfer coping), U.S. Pat. No. 5,213,502 (impression coping), U.S. Pat. Nos. 5,040,983, 4,861,767, 4,797,100, 4,698,021, 4,676,751, 4,492,579, 4,459,112, 3,685,114, re33,796, 4e33,2721, re 33,099, and the like. The entire disclosure of each of these United States patents is hereby incorporated by reference into this specification.

As will be apparent to those skilled in the art, the dental coping can be made into a spherical or partially spherical shape. Alternatively, the dental coping can be made into the cross-sectional shape of a tooth (at the gumline).

Referring to FIG. 9, and in the preferred embodiment illustrated therein, it will be seen that healing ball 160 preferably is comprised of an inwardly-extending annular protuberance 166 which is adapted to fit within and removably secured to annular groove 26. There thus is a strong fit between the mating hexagonal portions and the mating annular portions of healing ball 160 and abutment 10.

In many cases, the healing abutment ball 160 is removed from abutment 10 prior to the time any dental device is attached. In some instances, however, it is desired to attach the dental device directly to the healing ball 160. In this latter case, it is sometimes desirable to more securely attach the healing ball 160 to the abutment 10.

Figure 9A:
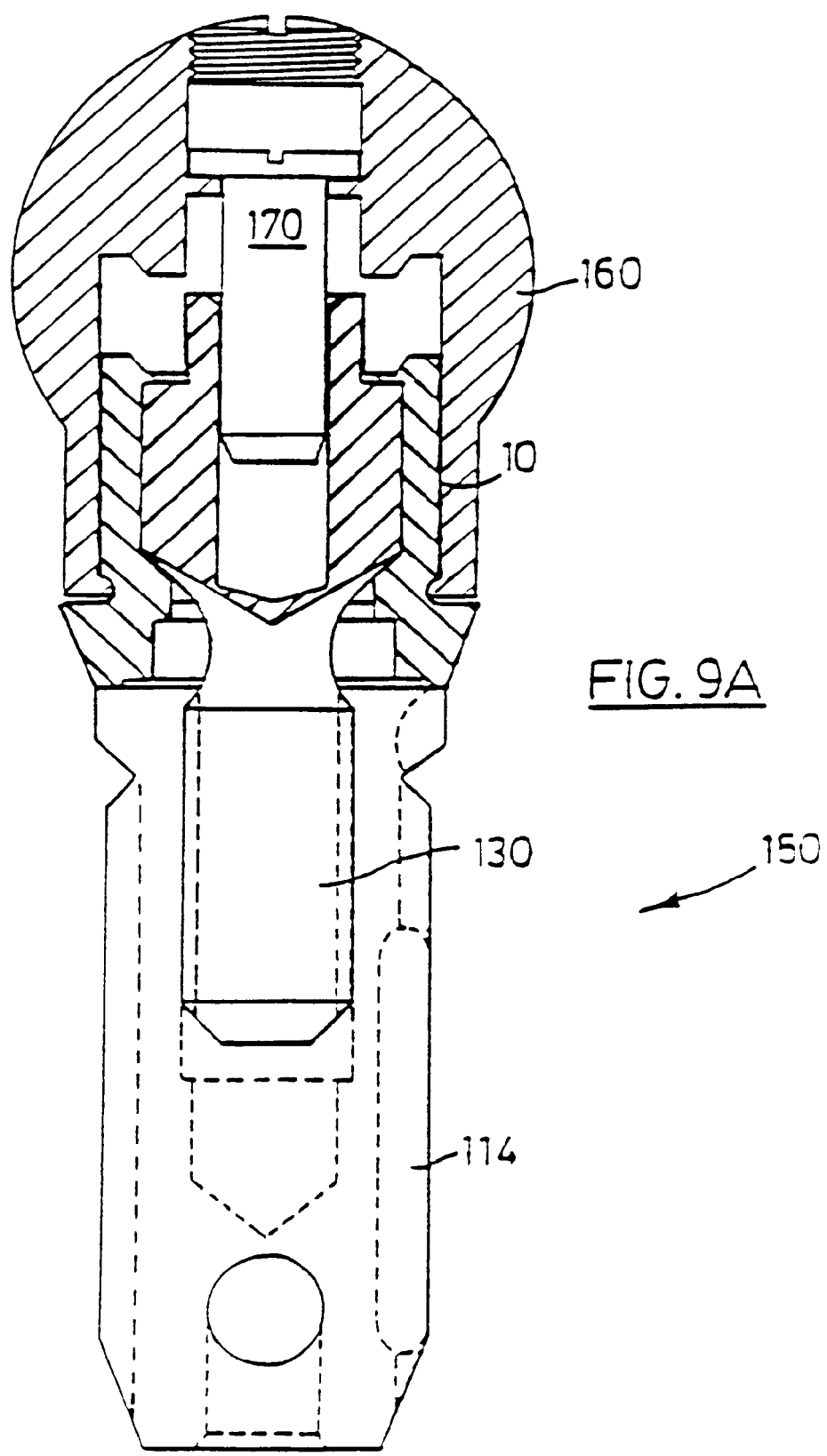
FIG. 9A is a sectional view illustrating another embodiment of the healing abutment connected to applicant's abutment/implant system.

One means of more securely making such attachment is illustrated in FIG. 9A. Referring to FIG. 9A, it will be seen that a screw 170 may be inserted through healing ball 160 into abutment retaining screw 130.

Figure 10:
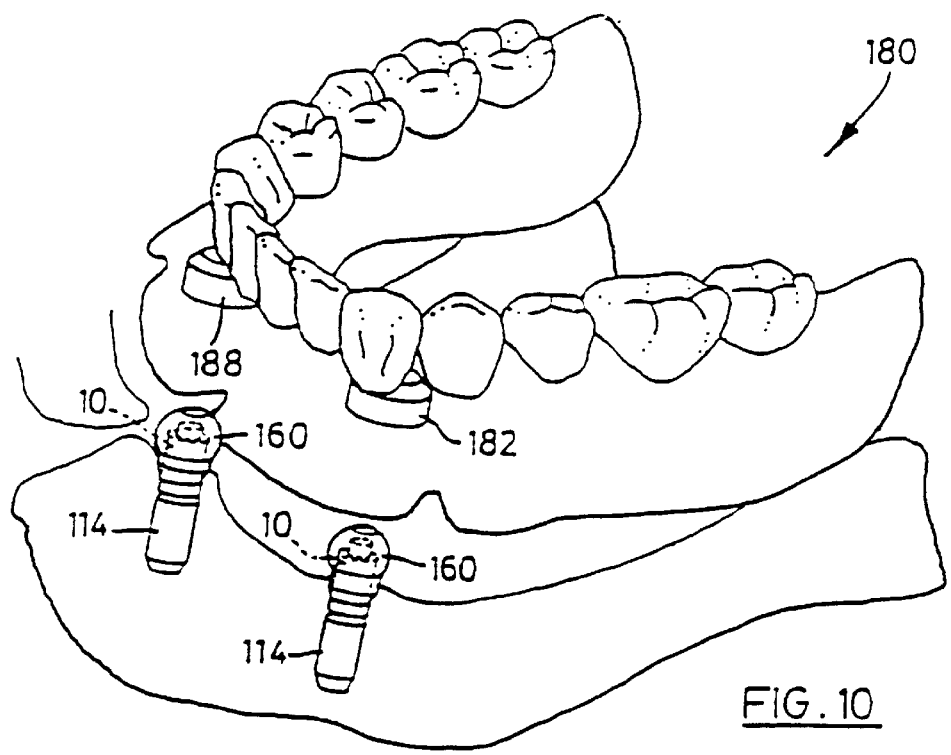
FIG. 10 is a perspective view of a denture connected to the healing abutment/abutment/implant system of FIG. 9 by means of O-rings.

FIG. 10 illustrates a denture 180 into which two metal rings 182 and 184 with O-rings 186 and 188 have been cured into the denture chairside. Such dentures are well known to those skilled in the art and are illustrated on page 21 of the aforementioned Nobelpharma catalog. Furthermore, Nobelpharma also sells an "Overdenture Kit for Ball Attachment" (see page 21 of the catalog) which contains a plastic cap with a rubber O-ring, ball attachment replicas, and spacers for the ball attachment.

Referring again to FIG. 10, it will be seen that the metal ring/O-ring assemblies are friction fit over the healing balls 160 to firmly and securely removably attach the denture 180 to the implant assembly.

FIG. 11 illustrates how the implant assembly 150 may be used in a similar manner with a gold cylinder 190. Such a gold cylinder is well known to those skilled in the art. See, for example, U.S. Pat. No. 5,209,659 (gold cylinder 126), U.S. Pat. No. 5,108,288 (coping 50 having a bore 52 passing axially therethrough and opening into a polygonal opening at its lower end), U.S. Pat. No. 5,145,371, and the like. The disclosure of each of these United States patents is hereby incorporated by reference into this specification.

Figure 12:
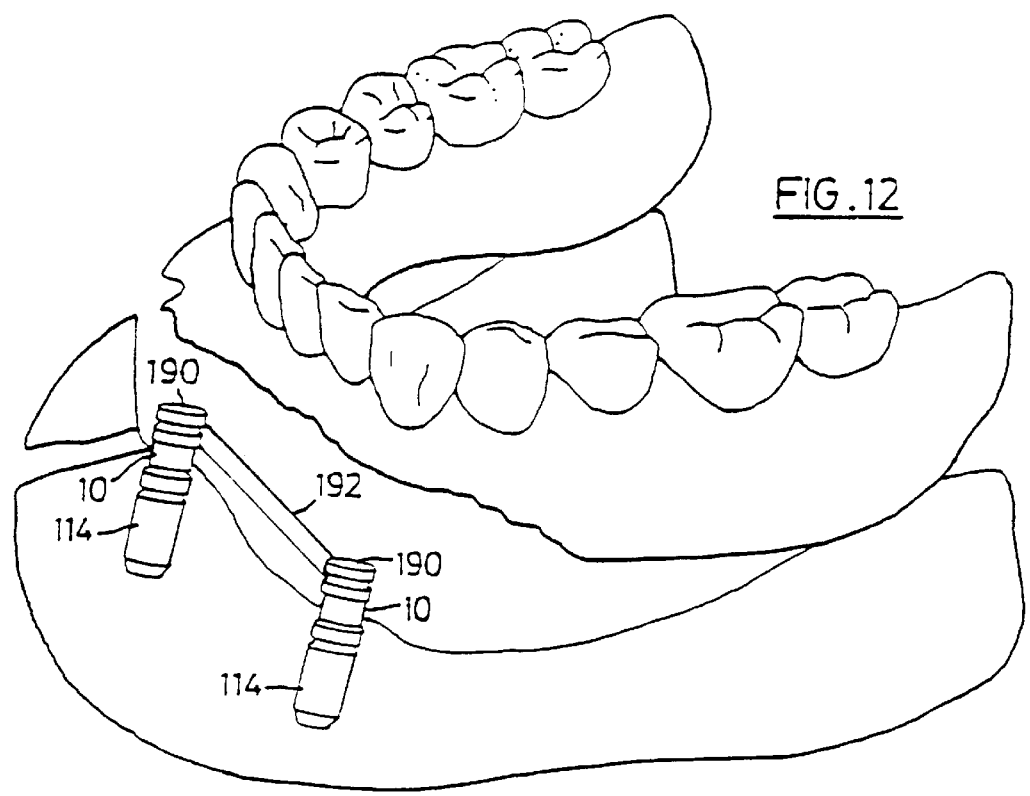
FIG. 12 is a perspective view of the assembly of FIG. 11 connected via a bar and clip to a denture in a patient's mouth.

It is known that gold cylinders are available for the fabrication of bar/clip overdentures, for they are designed to fit accurately on the hex abutments and can be incorporated into the bar/clip framework; see FIG. 12, and the bar clip assembly 192 illustrated therein. As will be apparent to those skilled in the art, this type of over-denture bar system may be readily connected to implant assemblies 150 attached to gold cylinders 190 (see FIG. 11).

Thus, as will be apparent to those skilled in the art, applicant's abutment 10, because of the relative universality of its design, may be used in conjunction with many different types of prosthetic applications. It thus affords the dental practitioner substantially more flexibility than does the prior art systems, which utilize a substantial number of parts which are adapted for specific applications.

Figure 13:
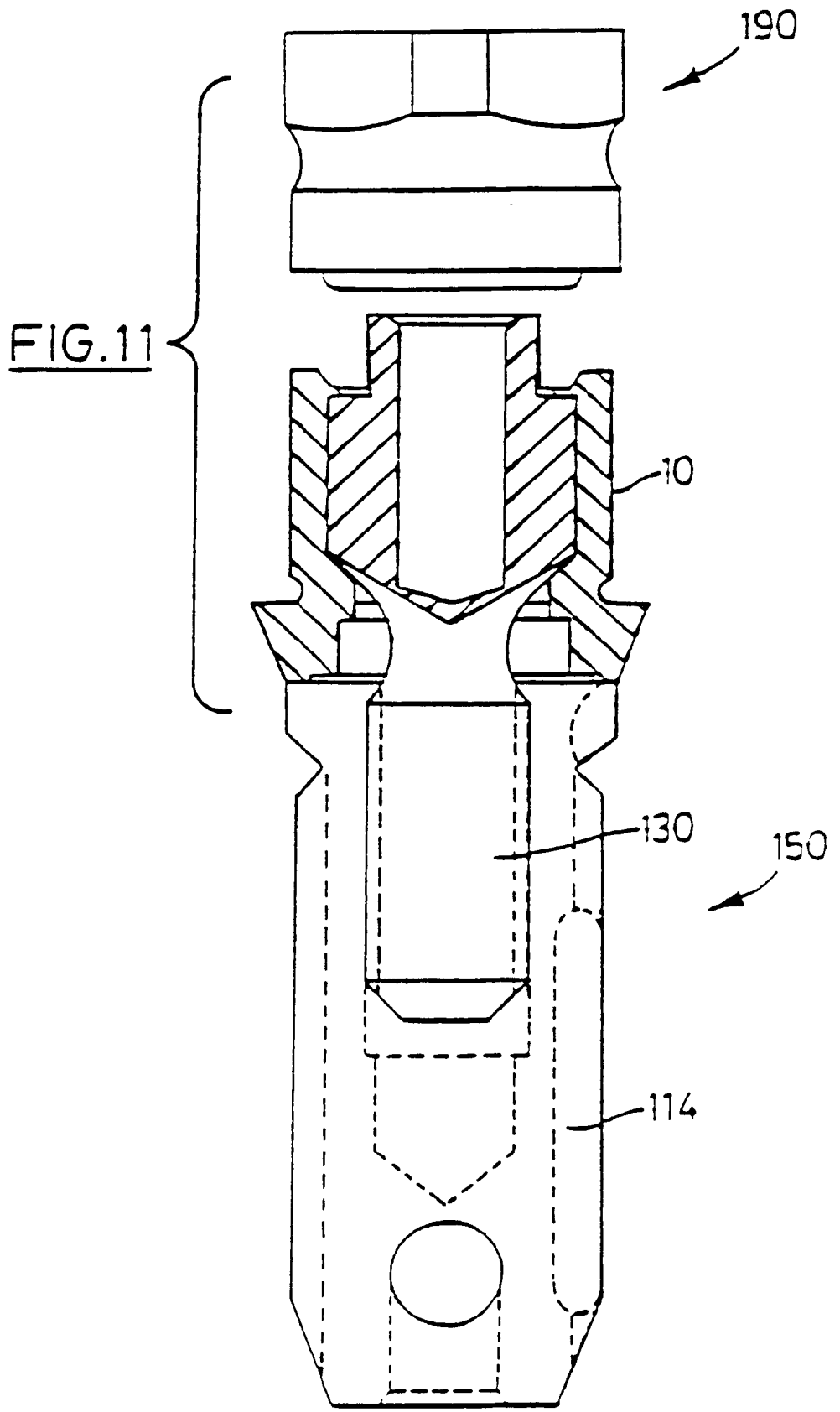
FIG. 13 is a perspective view of a fixed detachable implant supported bridge which utilizes applicant's abutment system.

Thus, by way of further illustration, and referring to FIG. 13, the gold cylinder devices 190 may be incorporated into a fixed detachable implant supported bridge 200. See, e.g., U.S. Pat. No. 5,174,954, the entire disclosure of which is hereby incorporated by reference into this specification.

Referring again to FIG. 13, it will be seen that screws 202 may be used to secure the bridgework through the gold cylinders to the abutments 10.

FIG. 14 is a perspective view of a gold coping 210 which may be utilized to restore a tooth to a patient's mouth. Referring to FIG. 14, it will be seen that gold coping 210 is comprised of an internal hexagonal bore 212 adapted to fit over and engage with hexagonal portion 24 of abutment 10 (see FIG. 15). As will be apparent to those skilled in the art, when gold coping 210 is placed on abutment 10, there are only six positions it can be in. By comparison, with prior art abutments which have cylindrical outer surfaces, there are an infinite number of such positions.

This system thus has several advantages. Because the gold coping 210/abutment 10 connection is locked into place by the interaction of the hexagonally-shaped parts, a patient cannot cause the tooth attached to abutment 10 to rotate upon application of pressure to the tooth. In the second place, the gold coping 210 can be utilized as a transfer coping during impression taking and, when so used, because of the interaction of the hexagonal shapes, accurately reproduces the position of abutment 10 in the working model.

Referring again to FIG. 14, it will be seen that, in the preferred embodiment illustrated therein, gold coping 210 has a substantially rectilinear top shape 214 with rounded corners 216. In one embodiment, the top of gold coping 210 is substantially square-shaped with rounded corners.

Referring again to FIG. 14, it is preferred that gold coping 210 comprise a multiplicity of annular grooves 218. Gold coping 210 also is comprised of stepped bores 220 and 222.

The gold copying 210 preferably consist essentially of a palladium alloy such as, e.g., the alloy disclosed in U.S. Pat. No. 5,174,954, the entire disclosure of which is hereby incorporated by reference into this specification. Thus, e.g., one may use a palladium alloy containing from about 50 to about 90 weight percent of palladium, from about 0 to about 37 weight percent of gold, from about 0 to about 3 weight percent of platinum, from about 0 to about 35 weight percent of silver, from about 0.5 to about 8 weight percent of gallium, from about 0 to about 8 weight percent of tin, and up to about 0.2 weight percent of a material selected from the group consisting of iridium, rhenium, ruthenium, and mixtures thereof.

Referring again to FIG. 14, it is preferred that the bottom portion 224 of gold coping 210 be adapted to mesh with a fit onto ledge 22 of abutment 10 (see FIG. 1).

Figures 15, 16:
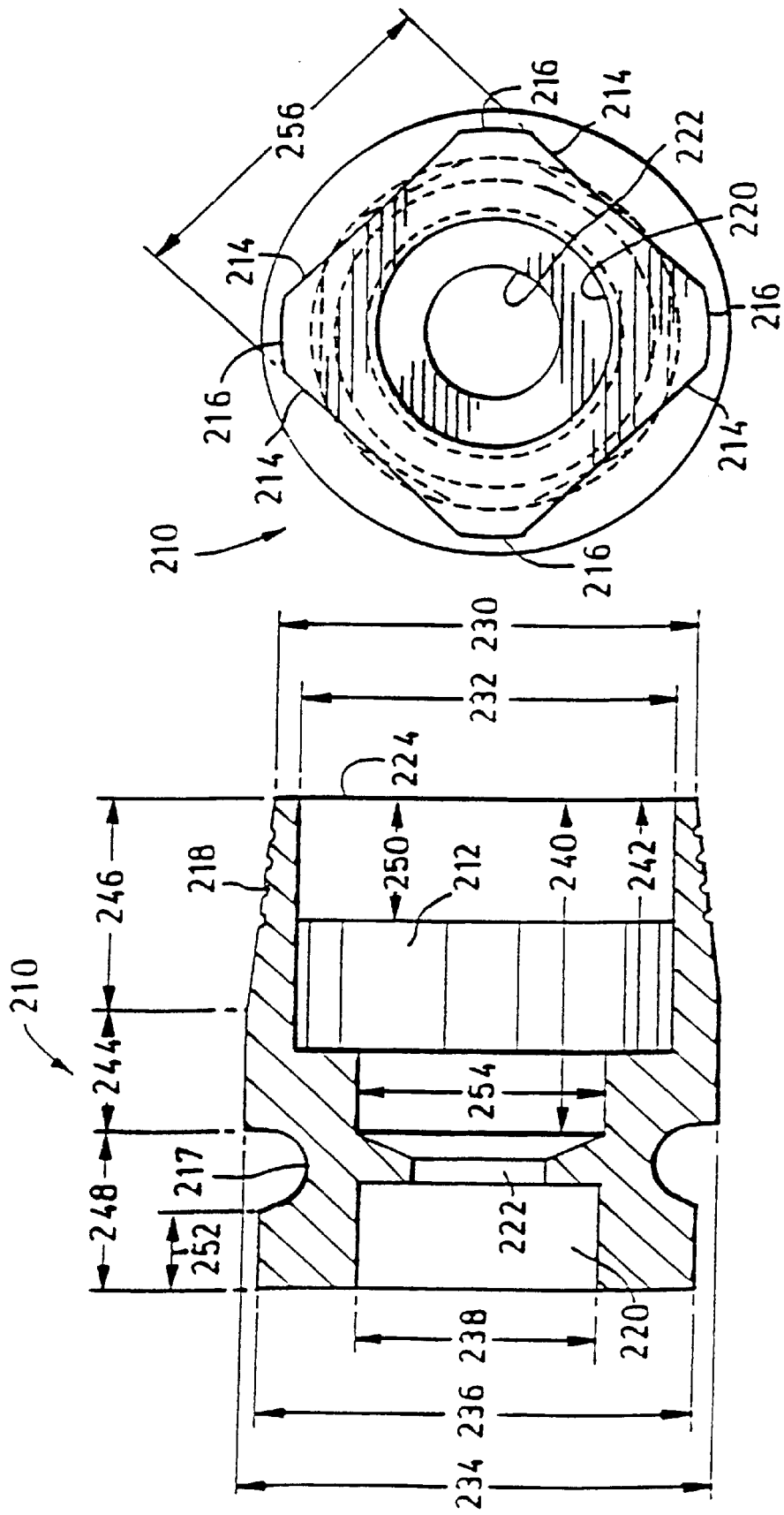
FIG. 15 is a sectional view of the gold coping device of FIG. 14.
FIG. 16 is a top view of the gold coping device of FIG. 14.

FIG. 15 is a sectional view of the gold coping device of FIG. 14. Referring to FIG. 15, and also to FIG. 14, it will be seen that gold coping 210 is comprised of a curved neck portion with a radius of curvature of about 1.5 millimeters.

In the preferred embodiment illustrated in FIG. 15, it will be seen that distance 230 is preferably 4.7 millimeters, distance 232 is preferably 4.2 millimeters, distance 234 is preferably 5.2 millimeters, distance 236 is 4.6 millimeters, distance 238 is 2.7 millimeters, distance 240 is 4.1 millimeters, distance 242 is 3.1 millimeters, distance 244 is 1.5 millimeters, distance 246 is 2.5 millimeters, distance 248 is 2 millimeters, distance 250 is 1.5 millimeters, and distance 252 is 1.5 millimeters, and distance 254 is 2.8 millimeters.

FIG. 16 is a top view of the gold coping of FIG. 14. Referring to FIG. 16, it will be seen that the distance 256 from opposing flat surfaces 214 is 4.0 millimeters.

FIG. 17 is an exploded perspective view illustrating how a tooth to which a gold coping 210 has been bonded may be attached to a patient's jawbone (not shown) by means of the abutment system of this invention.

Referring to FIG. 17, and in the preferred embodiment depicted, it will be seen that tooth 270 may be secured to abutment 10 by at least two separate means.

In the first place, a screw 272 may be inserted through orifice 22 and secured to retaining screw 130 by engagement with internal threads 134 (not shown in FIG. 17, but see FIG. 6A).

In the second place, dental cement may be charged into the interior of gold coping 210 prior to the time the gold coping 210 is placed over the hexagonal portion 24 of abutment 10. Thus, in addition to the mechanical bond created by screw 272, there also is an adhesive bond.

Furthermore, there is yet another bond tending to maintain gold coping 210 in position vis-a-vis abutment 10, and that is the interaction of their respective hexagonal shapes.

The system depicted in FIG. 17 has the unique advantage that allows the removal of the tooth 270 from the abutment 10 even after the cement has hardened. In order to do this, screw 272 may be removed by turning it counter-clockwise, and thereafter, utilizing a three-pronged crown-remover to pull tooth 270 out of the abutment 10 by leverage between the top of retaining screw 130 against the smaller taper of 270.

A Preferred Process of the Invention

Figure 18:
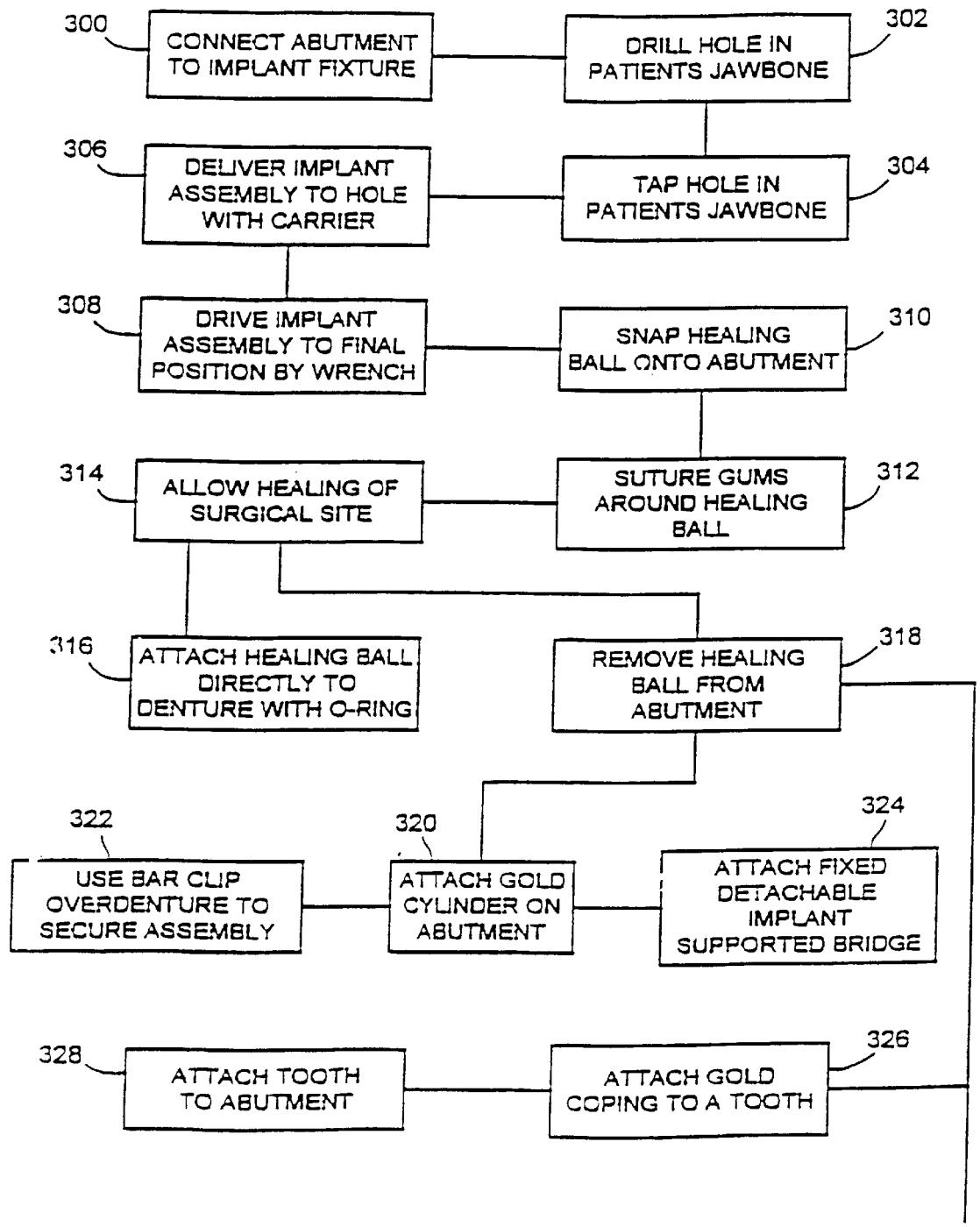
FIG. 18 a flow diagram illustrated certain preferred processes of the invention.

FIG. 18 is a flow diagram of one preferred process of applicant's invention.

In the first step of this process, step 300, abutment 10 is connected to implant fixture 114.

In this step, it is preferred to apply a torque no greater than about 20 Newton/centimeter.

Thereafter, in step 302 of the process, a hole is drilled in the jawbone of the patient sufficiently deep to receive only the length of the implant fixture. In general, this hole is usually from about 8 to about 18 millimeters.

Thereafter, in step 304 of the process, the hole thus drilled is preferably tapped with a tapping tool such as, e.g., the screw taps illustrated on page 11 of the Nobelpharma catalog.

Thereafter, in step 306 of the process, the abutment/implant fixture assembly is delivered to the hole by means of the carrier 90. The carrier 90 may also be used to start screwing the assembly into the hole, applying downward pressure while turning the assembly.

Generally, the carrier 90 will only enable one to drive the abutment/implant fixture assembly a portion of the required distance. The job may be finished by a power-driven socket wrench in step 308 of the process.

In the next step of this preferred process, step 310, the healing ball 160 is preferably snapped onto the abutment 10 (see FIGS. 9 and 9A). In one preferred embodiment, the healing ball 160 is disposed within compartment 101 of carrier 90 prior to its use.

Thereafter, in step 312, the gum tissue where the hole had been drilled is sutured around the healing ball 160.

In the next step of process, step 314, the surgical site is allowed to heal before the abutment 10 is directly or indirectly connected to a denture. In general, a healing period of from about 3 to about 6 months is desirable.

After the desired time of healing, no additional surgical procedure is required, unlike the prior art process (which necessitated second stage surgery to remove the cover screw used in the process and to attach the prosthetic abutment).

By comparison with prior art processes, applicant's prosthetic abutment is already attached.

At this stage of applicant's process, several options are available.

In one embodiment, illustrated in step 316 (also see FIG. 10), the healing ball is attached directly to a denture into which metal caps with an O-ring have been cured.

In another embodiment, illustrated in step 318, the healing ball 160 is removed from the abutment 10. At this stage, several additional options are available.

One such option is to attach the gold cylinder 190 on the abutment 10 (see FIGS. 11 and 12) in step 320. Once the gold cylinder 190 has been so attached, one may prepare a bar clip overdenture (see FIG. 12) and attach such denture to the superstructure (see step 322). Alternatively, in step 324, the gold cylinders 190 can be incorporated into a fixed detachable implant supported bridge and thereafter secured to multiple implants in place in the jawbone (see FIG. 13).

Alternatively, in step 326, after the healing ball 160 has been removed a gold coping 210 may be attached to a tooth (see,e.g., FIG. 17 where such a gold coping is imbedded in the tooth). Thereafter, in step 328, such tooth is attached to the abutment 10.

An Integral Implant Assembly

Figure 19:
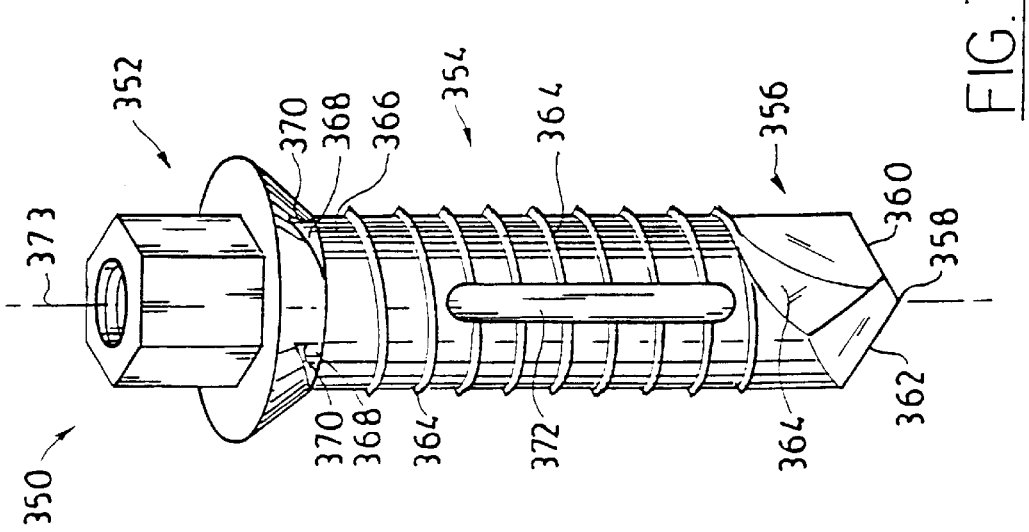
FIG. 19 is a perspective view of one embodiment of an implant assembly comprised of the abutment similar to the one depicted in FIG. 1 integrally joined to a dental implant having cutting means.

FIG. 19 is a perspective view of a preferred embodiment of an implant device 350 which is comprised of an abutment 352 integrally connected to an implant 354.

Referring to FIG. 19, it will be seen that implant device 350 is comprised of several cutting means. One such cutting means is integrally formed drill bit 356.

Drill bit 356 is preferably integrally joined to implant section 354 and is adapted to drill bone. Any of the drill bit configurations known to those skilled in the art to useful in drilling bone may be used as drill bit 356. Thus, by means of illustration and not limitation, one may use one or more of the drill bit configurations depicted in U.S. Pat. Nos. 5,443,468, 5,437,677 (drilling in the glenoid neck), U.S. Pat. Nos. 5,413,579, 5,409,489 (drilling in a femur), U.S. Pat. No. 5,403,322 (drilling in the bone of a human limb), U.S. Pat. Nos. 5,366,457, 5,354,299, 5,306,278 (corticotomy drill guide), U.S. Pat. Nos. 5,257,809, 5,055,105, D332492, D273326, and the like. The disclosure of each of these United States patents is hereby incorporated by reference into this specification.

Referring again to FIG. 19, and in the preferred embodiment depicted therein, it will be seen that drill bit 356 is comprised of a tip 358, a first blade 360, and a second blade 362, and a clearance channel 364. In one embodiment, not shown, drilling bit 356 is comprised of three blades.

In addition to the drill bit 356, implant assembly 350 also is comprised of raised external helical threads 364 which are disposed on a substantially cylindrical body portion 366. In one preferred embodiment, threads 364 and body portion 366 are similar to or identical to the threads 53 and body portion 52 of applicant's U.S. Pat. No. 5,338,197; the disclosure of this patent is hereby incorporated by reference into this specification.

In addition to the drill bit 356 and the threads 364, applicant's implant assembly also is comprised of a multiplicity of cutting means 368 such as, e.g., cutting flutes in the form of indented notches. In one preferred embodiment, illustrated in FIG. 19 (also see elements 70 and 70' of U.S. Pat. No. 5,358,197), each of the indented notches 368 has a radially outwardly-extending cutting surface 370 at substantially a right angle to the circumferential direction of rotation of the implant assembly 350 (see, e.g., axis 372).

In another embodiment, not shown, the drill bit 356 and/or the threads 364 are replaced, in whole or in part, by a self-tapping dental implant. One may use any of the self-tapping means disclosed in the art such as, e.g., those disclosed in U.S. Pat. No. 5,601,429 (self tapping threads), U.S. Pat. No. 5,571,017 (self tapping threads), U.S. Pat. No. 5,435,723 (self tapping threads), and the like. The disclosure of each of these United States patents is hereby incorporated by reference into this specification.

Referring again to FIG. 19, and in the preferred embodiment depicted therein, it will be seen that implant assembly 350 is comprised of a longitudinal channel 372 which is similar in function and structure to the longitudinal channel 84 depicted in applicant's U.S. Pat. No. 5,338,197.

As will be apparent to those skilled in the art, the device of FIG. 19 is comprised of abutment 352 joined to implant 354. However, other implants may also be integrally joined to abutment 352.

Figure 20:
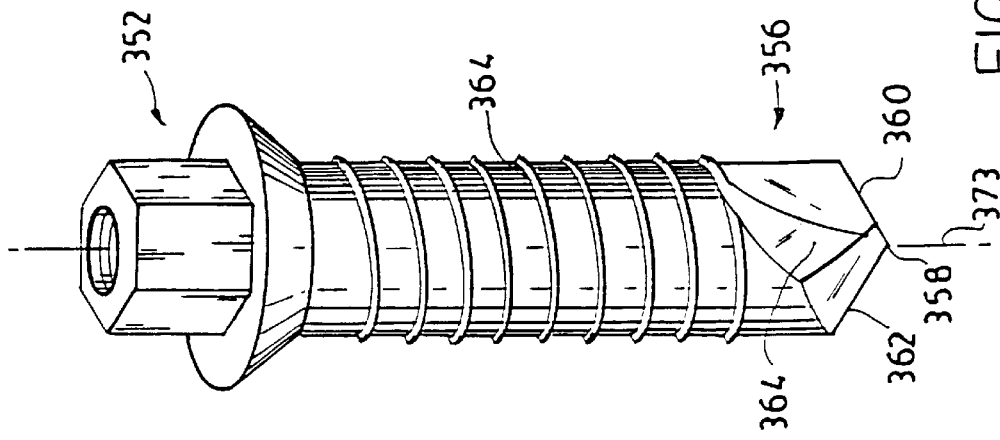
FIG. 20 is a perspective view of another embodiment of an implant assembly comprised of the abutment of FIG. 19 integrally joined to a dental implant having cutting means.

Thus, by way of further illustration, the implant device 380 depicted in FIG. 20 is very similar to the device 350 depicted in FIG. 19 but it omits the use of the longitudinal channel 372 and the cutting flutes 368. In another embodiment, not shown, the device incorporates the longitudinal channel 372 but not the cutting flutes 368. In another embodiment, not shown, the device incorporates the cutting flutes 368 but not the longitudinal channel 372. In another embodiment, not shown, the device omits the raised helical threads 364 and incorporates either both the cutting flutes 368 and/or the longitudinal channel 372 and/or the drill bit 356. Other variations and combinations will be apparent to those skilled in the art.

Figure 20A:
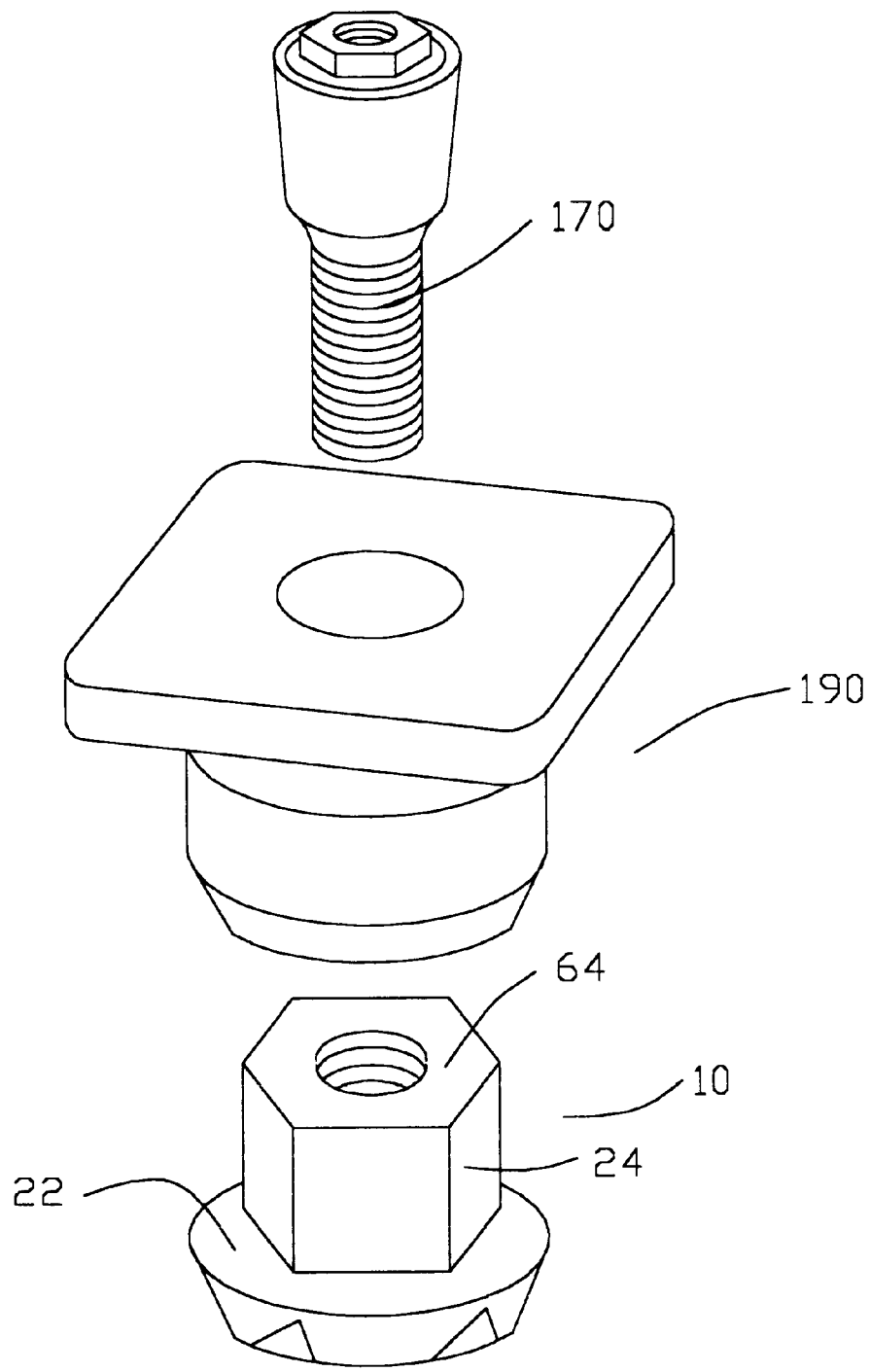
FIG. 20A is an exploded view of an implant assembly comprised of a gold cylinder 190 removably attached to an abutment.

One such embodiment is illustrated in FIG. 20A, which depicts a gold cylinder 190 removably attached by means of screw 170 to the abutment 10.

Figure 21:
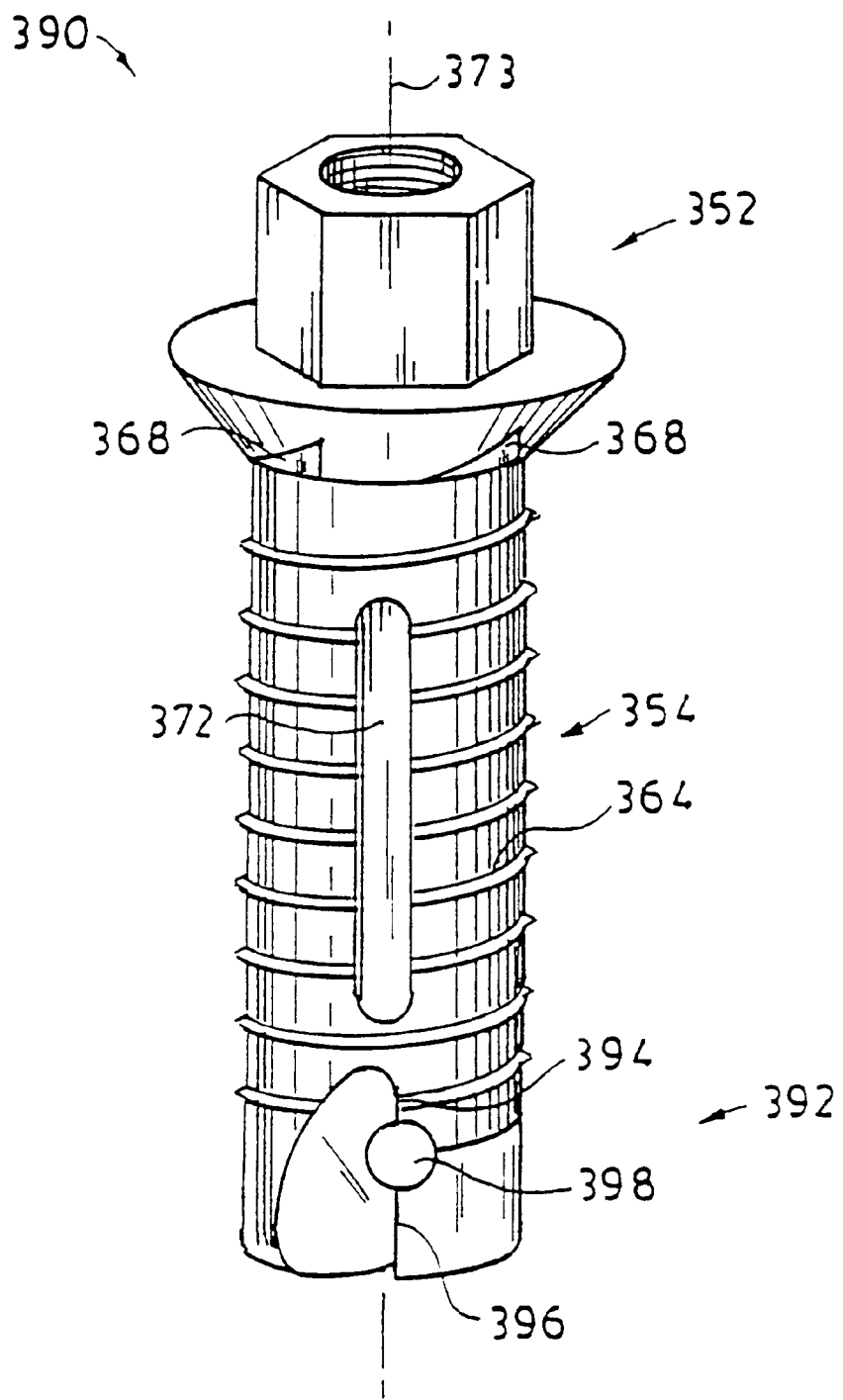
FIG. 21 is a perspective view of another embodiment of an implant assembly comprised of the abutment of FIG. 19 integrally joined to a dental implant having cutting means.

One preferred embodiment is disclosed in FIG. 21 as implant assembly 390. This implant assembly 390 is substantially identical to the implant assembly 350 (see FIG. 20) with the exception that the drill bit 356 is replaced by a bottom tapered portion 392 which is very similar to the cutting assembly depicted in U.S. Pat. No. 5,338,197.

Thus, referring to FIG. 21, it will be seen that tapered portion 392 is comprised of cutting surfaces 394 and 396 disposed at opposite ends of through-hole 398 and preferably perpendicularly disposed to the axis of rotation 372 such that the cutting surfaces 394 and 396 will both cut and direct all or a substantial portion of bone fragments into through-hole 398.

Figure 22:
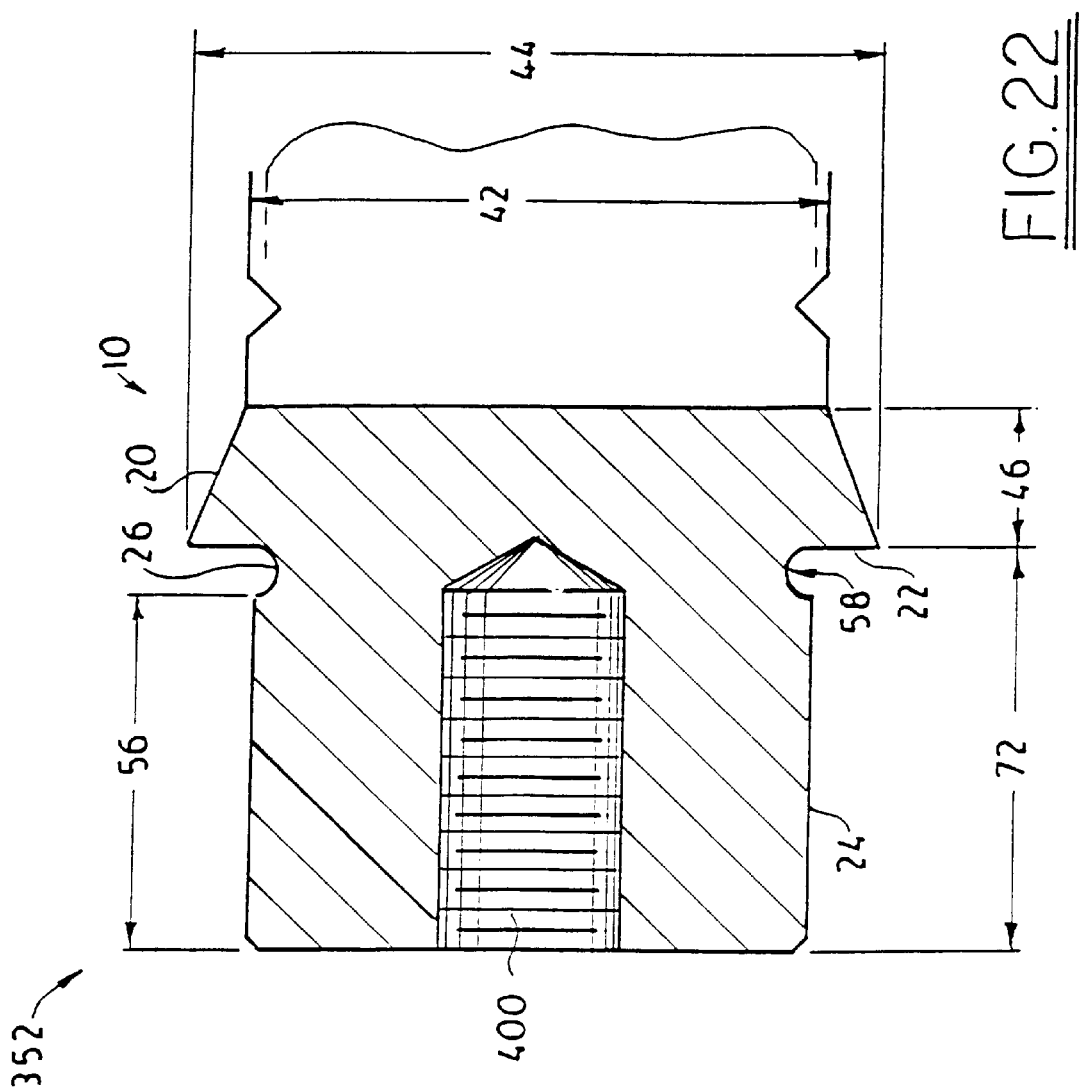
FIG. 22 is a sectional view of the preferred abutment depicted in FIGS. 19, 20, and 21.

FIG. 22 is a sectional view of abutment 352. As will be apparent to those skilled in the art, this abutment 352 is very similar to abutment 10 (see FIG. 1), but it differs therefrom in that does not contain a passageway with six stepped bores (see FIG. 2 for a depiction of these passageways in abutment 10).

By comparison, and referring to FIG. 22, it will be seen that abutment 352 is comprised is preferably comprised of a threaded orifice 400 which, preferably, has a substantially circular cross-sectional shape. As will be apparent to those skilled in the art, threaded orifice 400 is adapted to receive and retain a dental prosthesis (not shown).

Figure 22A:
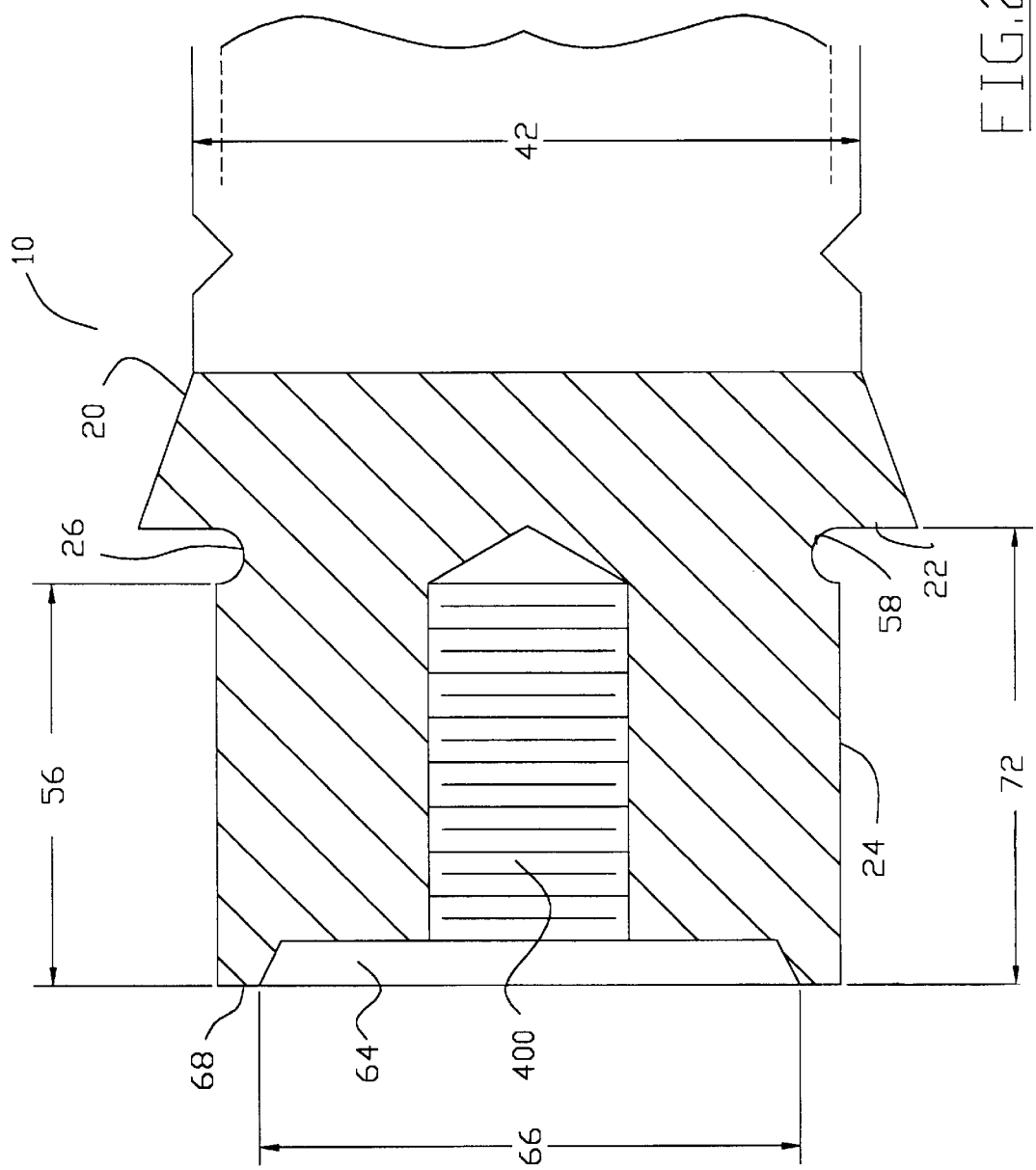
FIG. 22A is a sectional view of an abutment similar to that depicted in FIG. 22 with the exception that it contains a stepped bore 64 to receive a gold cylinder.

Referring again to FIG. 22, it is seen that base 20 of abutment 352 is tapered. This is advantageous in the retention of the implant assembly within the bone. FIG. 22A is a sectional view of a device similar to that depicted in FIG. 22 with the exception that it contains a stepped bore 64 to receive a gold cylinder 190 (not shown).

Referring again to FIGS. 19–22A, the implant devices depicted therein preferably consist essentially of alumina, titanium, titanium alloy, and/or other material which is biocompatible with human bone.

The integral implant assemblies of this invention may be used in a manner similar to the multi-piece assemblies. However, because of their integral structure, they are stronger than the multi-piece assemblies, less likely to disengage, and less likely to present opportunity for bacterial ingress from the oral cavity into the bone tissue.

Elsewhere in this specification, the use of healing ball 160 is disclosed in connection with its attachment to abutment 10. As will be apparent to those skilled in the art, healing ball 160 may also be removably attached to abutment 352 and, when such abutment is integrally connected to implant fixture 354, to implant devices 350, 380, and 390.

Figure 23:
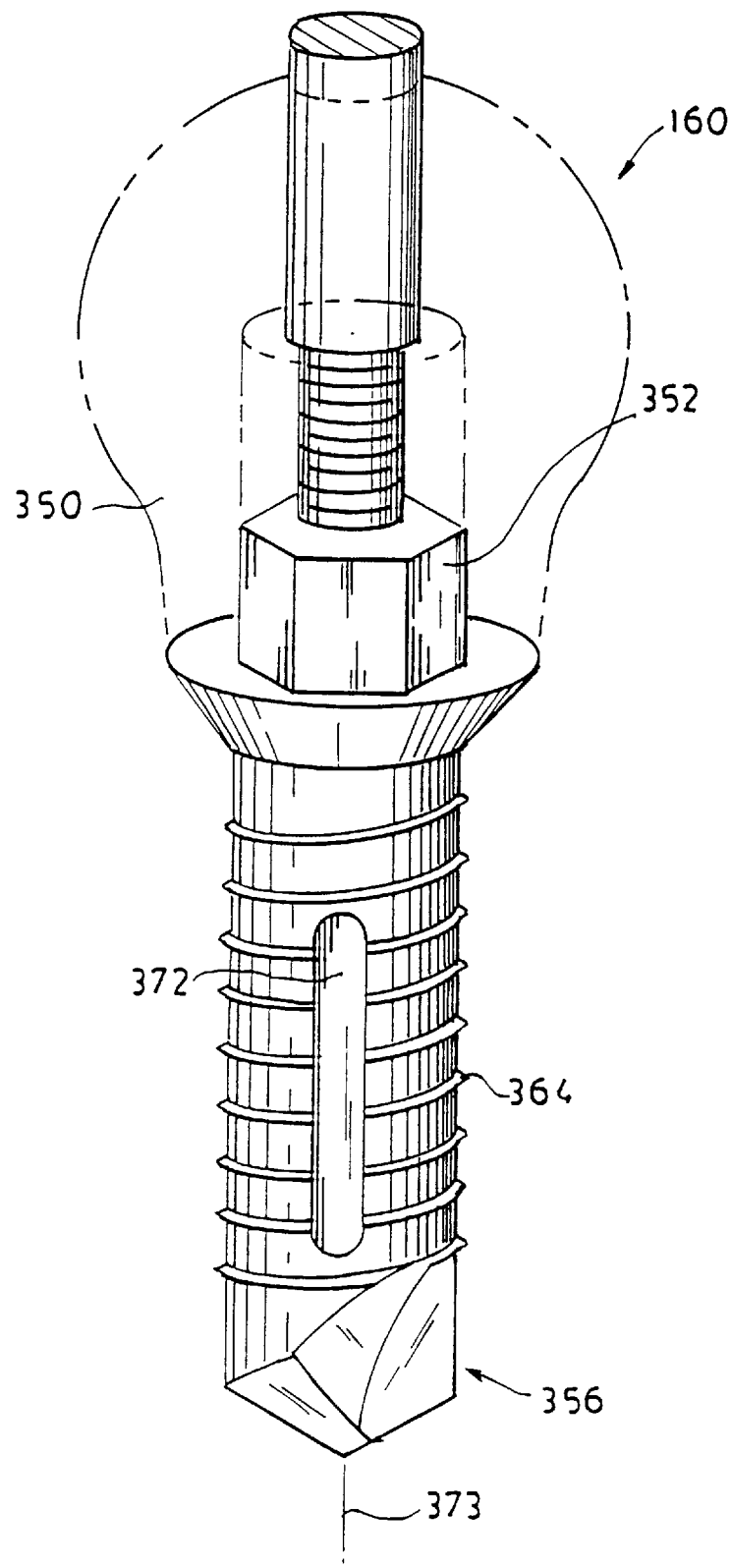
FIG. 23 is an exploded view illustrating the connection of the healing ball of this invention to the integral dental implant of FIG. 19.

FIG. 23 illustrates one such attachment in which, for the sake of simplicity of representation, the means by which annular protuberance 166 fits within annular groove 26 have been omitted (but see FIGS. 8, 9, and 10).

One substantial advantage of the system depicted in FIG. 23 is that, after coping 160 has been removably attached to removable dental implant 350, the entire assembly can be removed from the patient's mouth and transferred to a working model to fabricate the dental prosthesis.

In one preferred embodiment, not shown, coping 160 has a substantially hexagonal shape and preferably consists essentially of plastic. This embodiment is especially advantageous for allowing direct pick up of the assembly and accurate timed transfer to a working model. Thus, the expensive prior art cast-on technique can be avoided, as can the painful and time-consuming process of gingival retraction for impression taking.

Figure 24A:
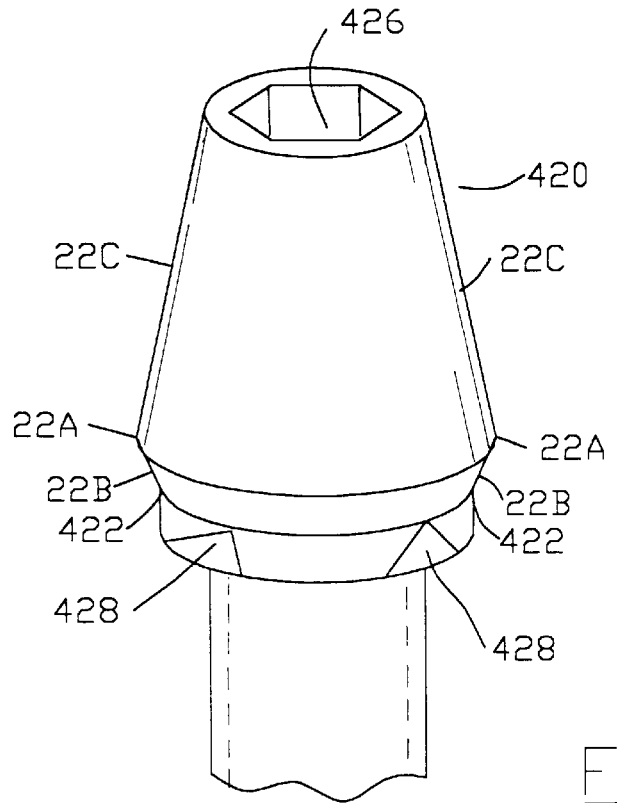
FIG. 24A is a partial perspective view of another preferred assembly of the invention.

FIG. 24A is a partial perspective view of an implant assembly 420 whose ridge 22A is formed at the intersection of walls 22B and 22C. The wall 22B extends upwardly and outwardly from base 422 and thereafter, after forming ledge 22A, extends upwardly and inwardly to the top 424 of the abutment. The orifice 426 in the abutment has a substantially hexagonal shape adapted to engage a correspondingly shaped instrument. Cutting means 428 are disposed about the periphery of base 422 (see, e.g., U.S. Pat. No. 5,338,197, the entire disclosure of which is hereby incorporated by reference into this specification).

Figure 24B:
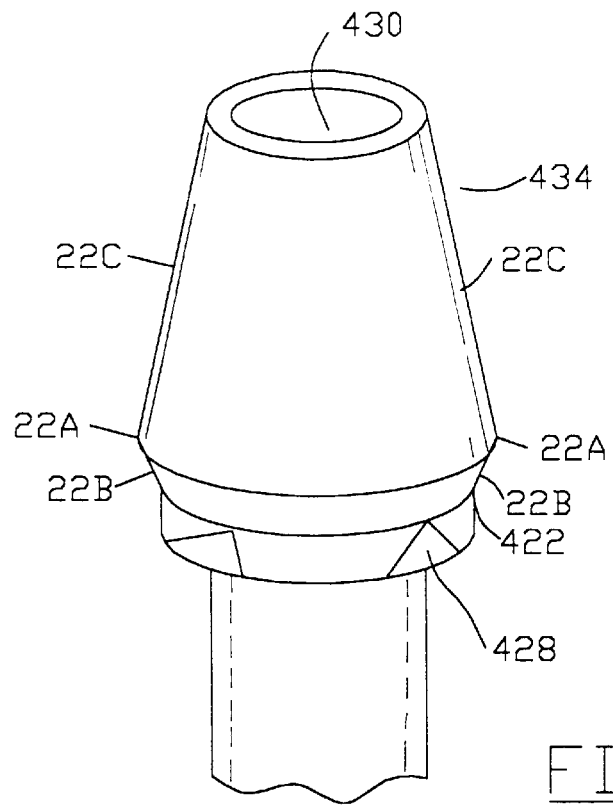
FIG. 24B is a partial perspective view of yet another preferred assembly of the invention.

FIG. 24B is partial perspective view of an implant assembly 434 which is similar implant assembly 420 with the exception that its orifice 430 has a different shape.

Figure 24C:
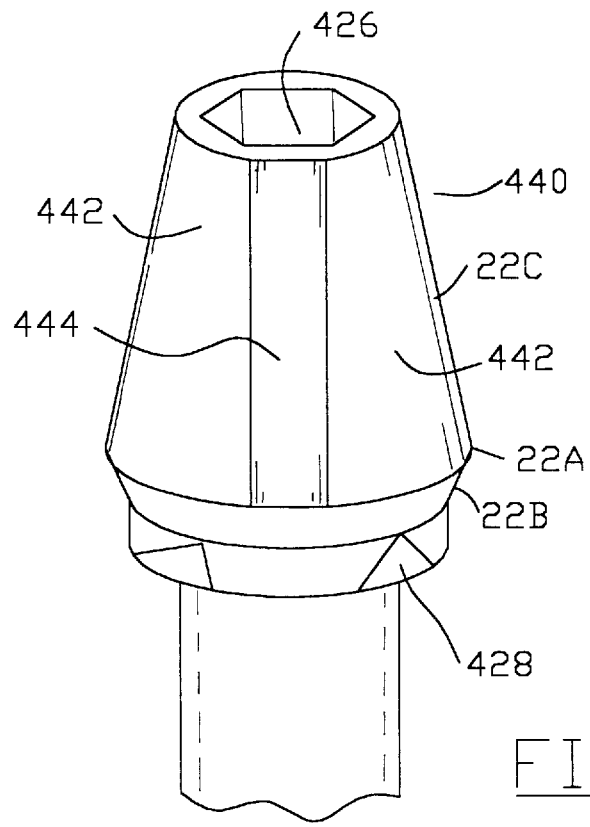
FIG. 24C is a partial perspective view of yet another preferred assembly of the invention.

FIG. 24C is partial perspective view of an implant assembly 440 which is similar to implant assembly 420 with the exception that it is comprised of alternating arcuate walls 442 and linear walls 444. In the embodiment depicted, linear wall 444 extends substantially the whole length of the abutment wall 22C. In another embodiment, not shown, linear wall extends less than the whole length of abutment wall 22C. It is preferred that linear wall 444 extend at least about 3 millimeters. It will be recognized by those skilled in the art that there often are a multiplicity of linear walls 444 and that these linear walls may extend to differing degrees from each other, or may extend to the same degree.

Figure 24D:
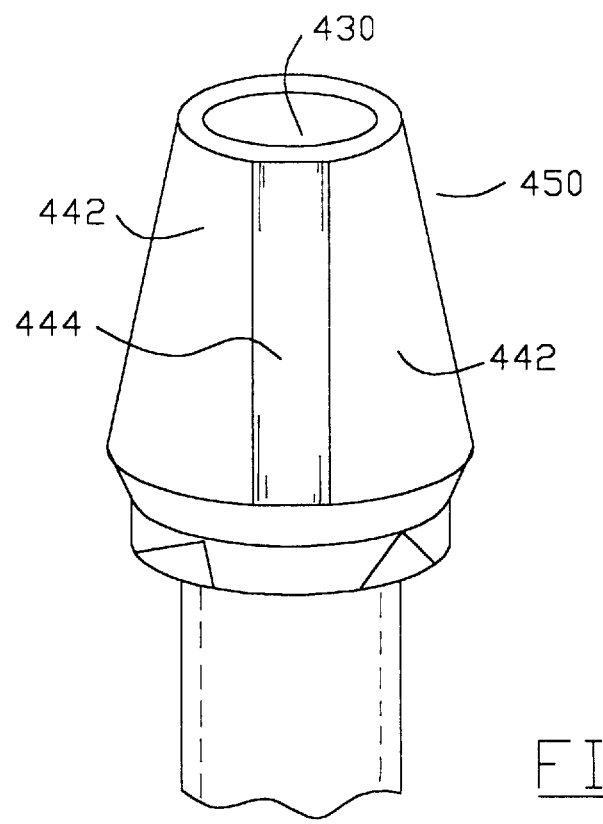
FIG. 24D is a partial perspective view of yet another preferred assembly of the invention.

FIG. 24D is partial perspective view of an implant assembly 450 which is similar to implant assembly 440 with the exception that it contains a substantially circular orifice 430.

Figure 24E:
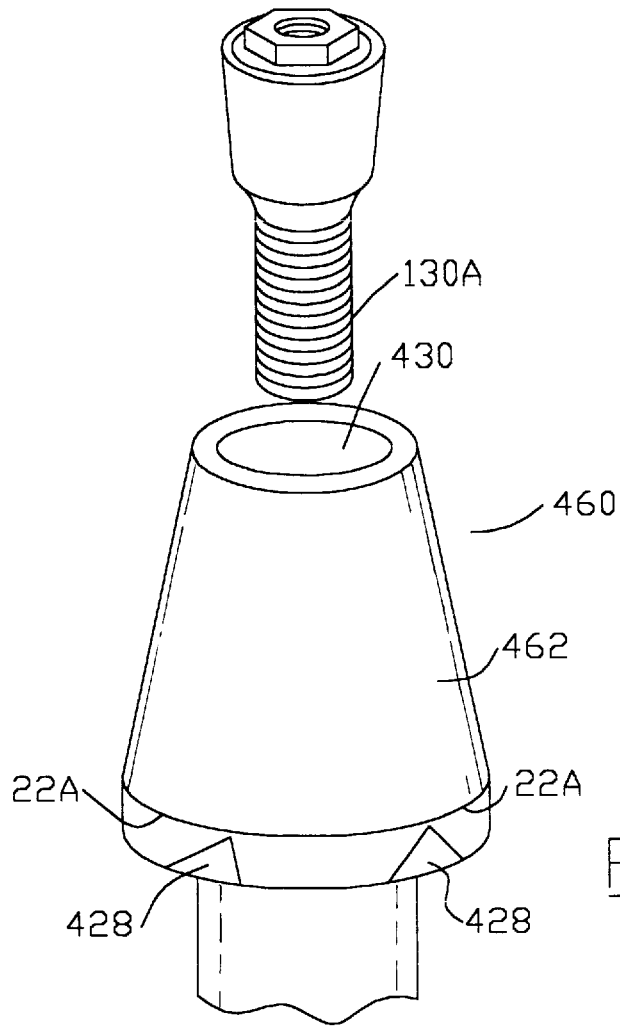
FIG. 24E is a partial exploded view of yet another preferred embodiment of the invention.
Figure 24F:
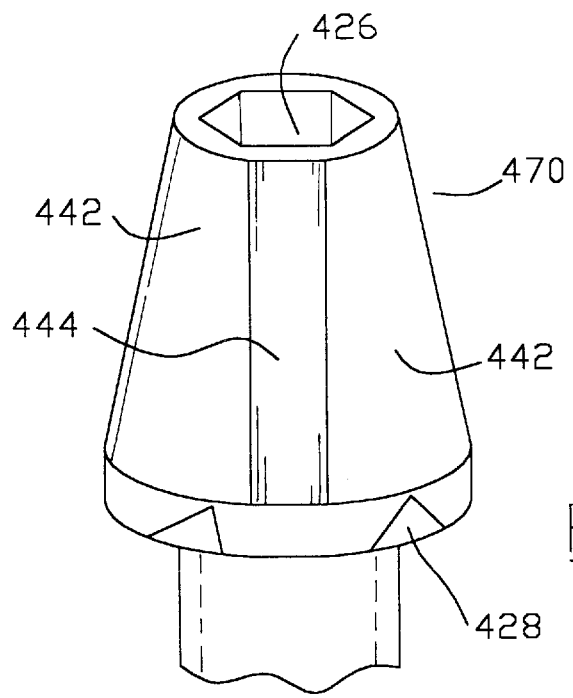
FIG. 24F is a partial perspective view of yet another preferred embodiment of the invention.

FIG. 24E is a partial perspective view of an implant assembly 460 comprised of an abutment screw 130A. In the embodiment depicted in this Figure, the ledge 22A is formed at the bottom of base 462.

Figure 24G:
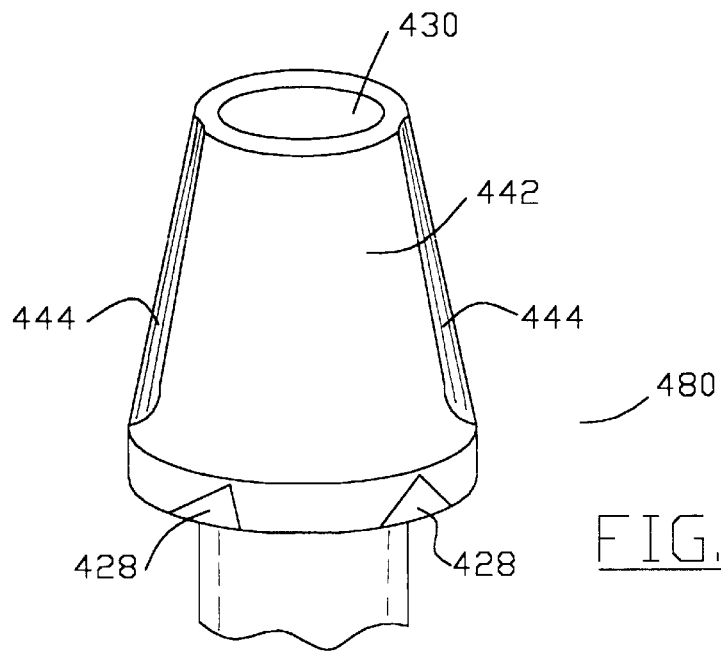
FIG. 24G is a partial perspective view of yet another preferred embodiment of the invention.

FIG. 24G is a partial perspective view of an implant assembly 480 which contains a substantially circular orifice 430 and alternating arcuate and linear walls 442 and 444.

Figure 24I:
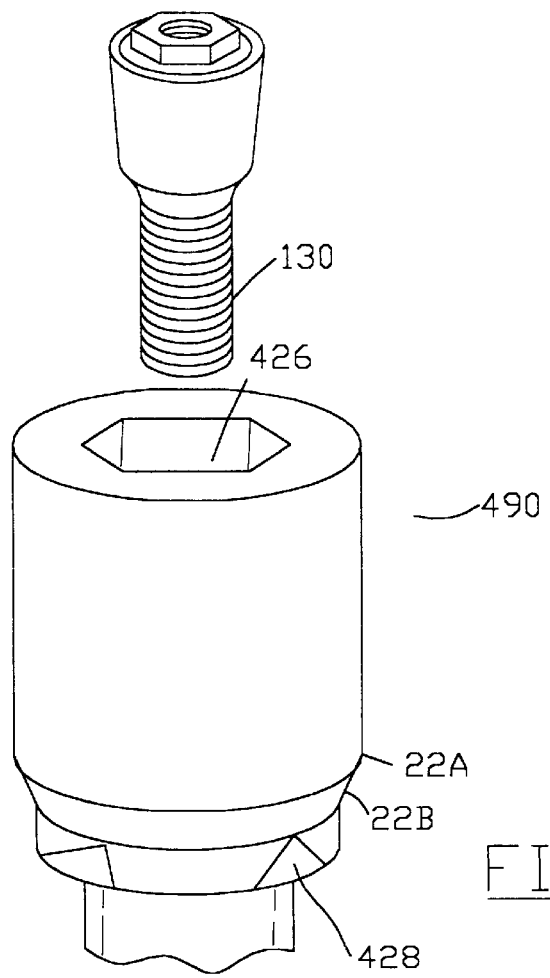
FIGS. 24I and 24J are partial perspective views of another preferred assembly of the invention with different internal orifices.
Figure 24J:
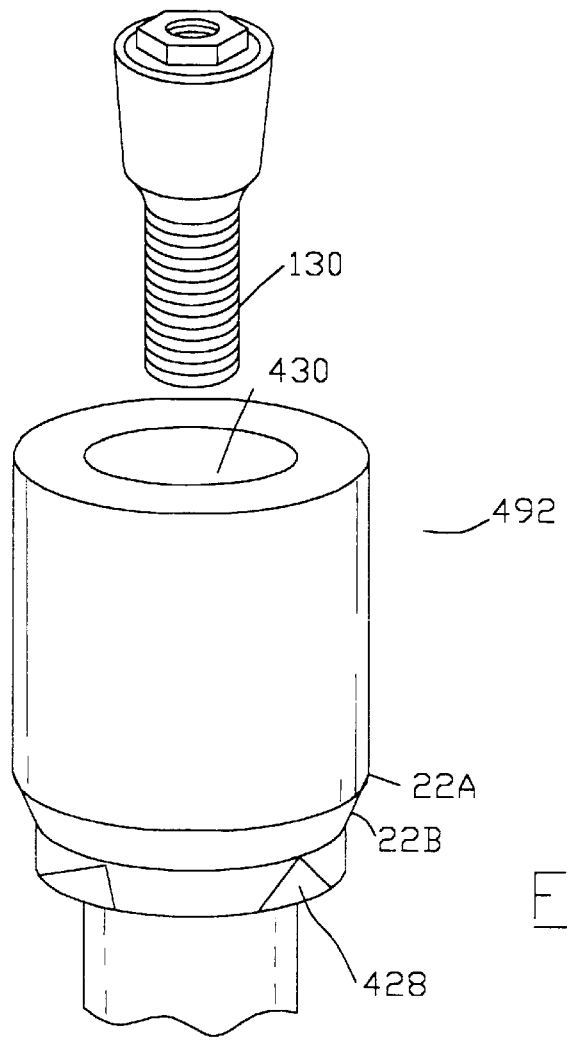

FIGS. 24I and 24J are partial perspective views of implant assemblies 490 and 492 whose walls 22B extend upwardly and outwardly until they form ledge 22A and thereafter extend substantially vertically and upwardly.

Figure 24K:
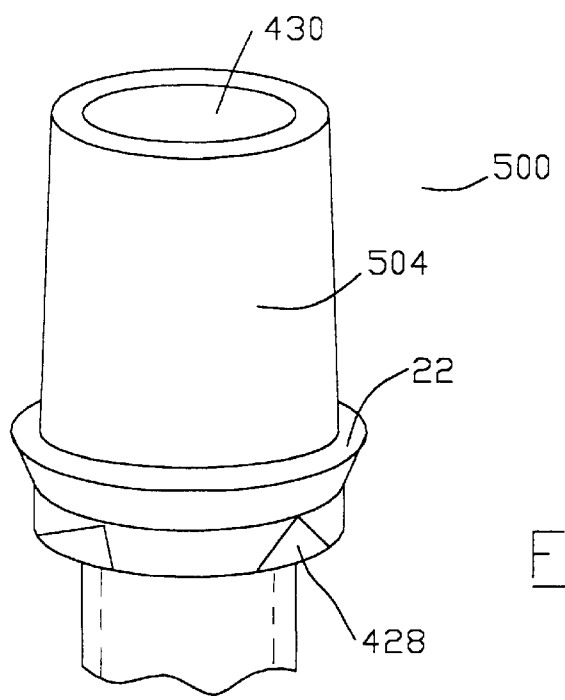
FIGS. 24K and 24L are partial perspective views of yet another preferred assembly with different orifices.
Figure 24L:
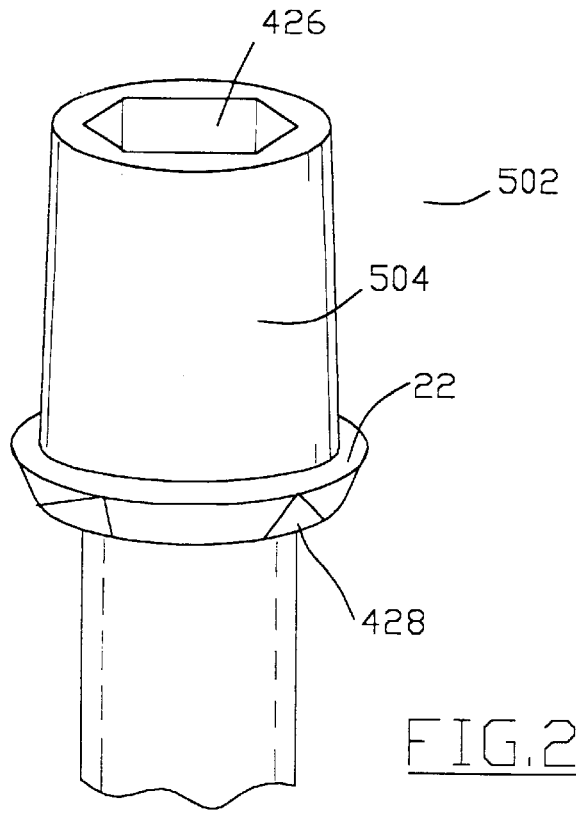

FIGS. 24K and 24L are partial perspective views of implant assemblies 500 and 502 in which the ledges 22 extend substantially horizontally. In the embodiments depicted, the wall 504 preferably has a substantially conical shape and extends upwardly in a tapered manner.

Figure 24M:
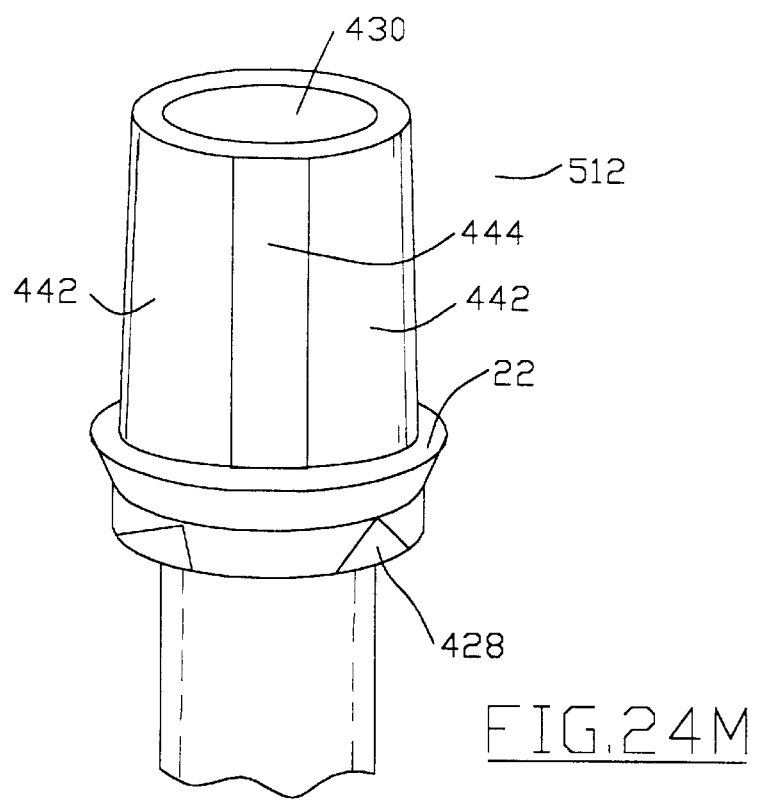
FIGS. 24M and 24N are partial perspective views of yet another preferred assembly of the invention with different orifices depicted.
Figure 24N:
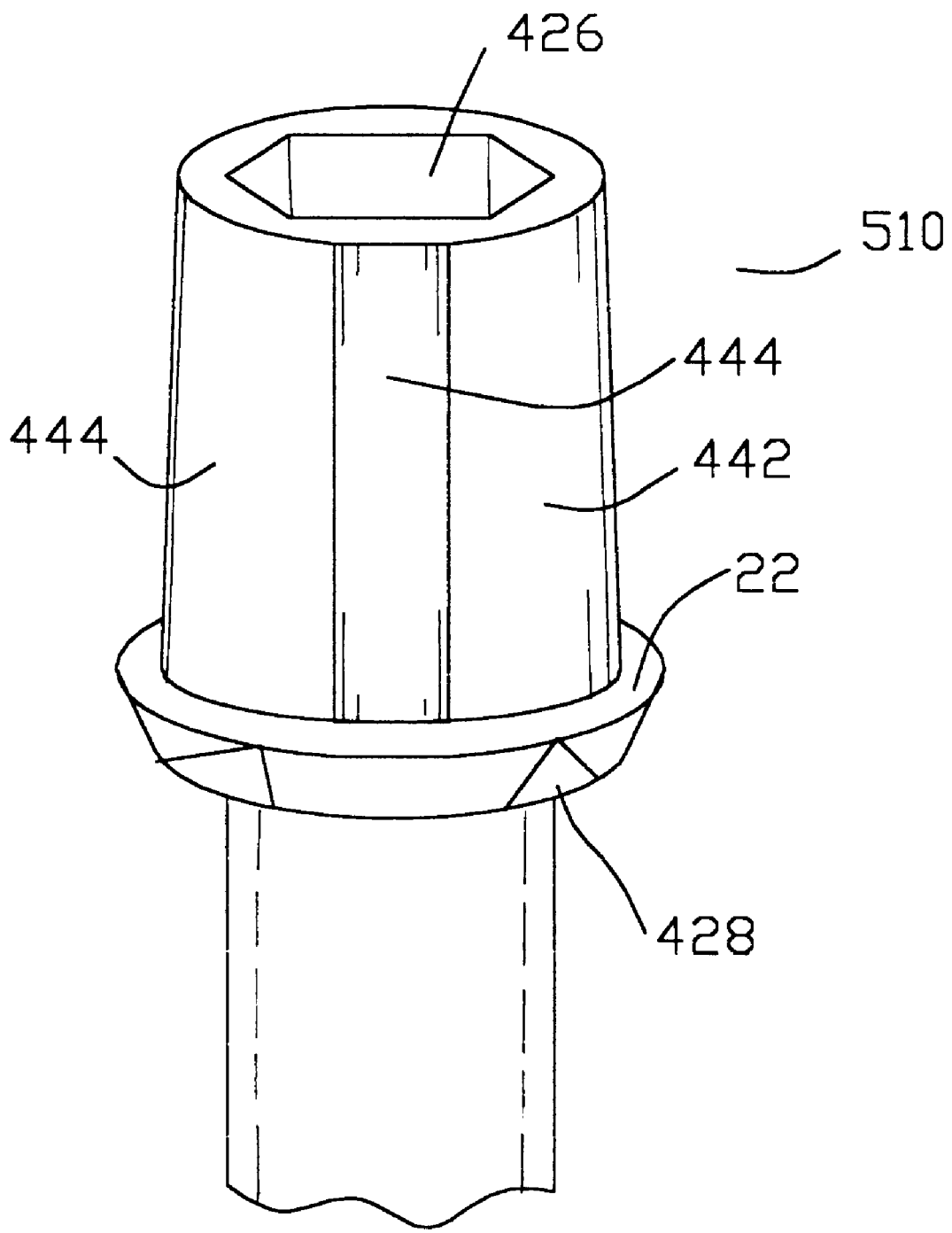

FIGS. 24N and 24M are partial perspective views of implant assemblies 510 and 512 which are substantially similar to assemblies 500 and 502 but differ therefrom in having alternating arcuate and linear walls 442 and 444.

Figure 25A:
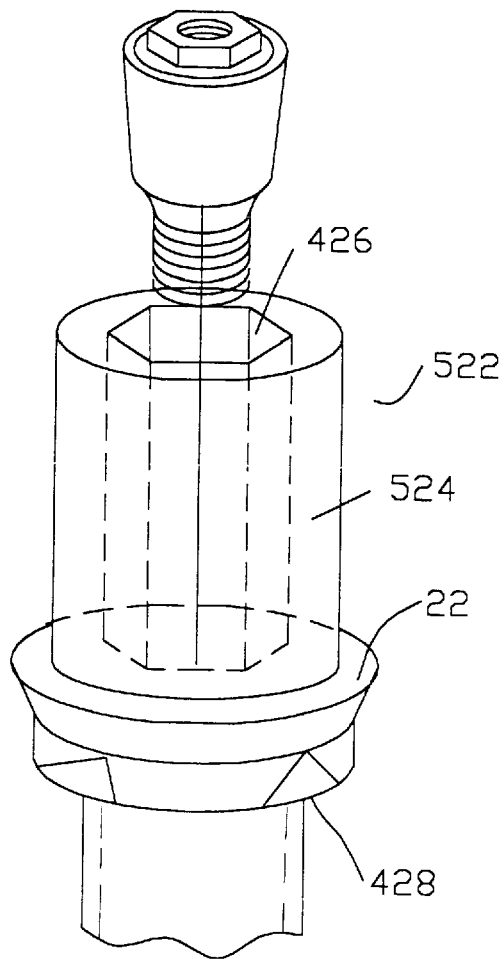
FIGS. 25A and 25B are partial perspective views of yet another preferred assembly of the invention.
Figure 25B:
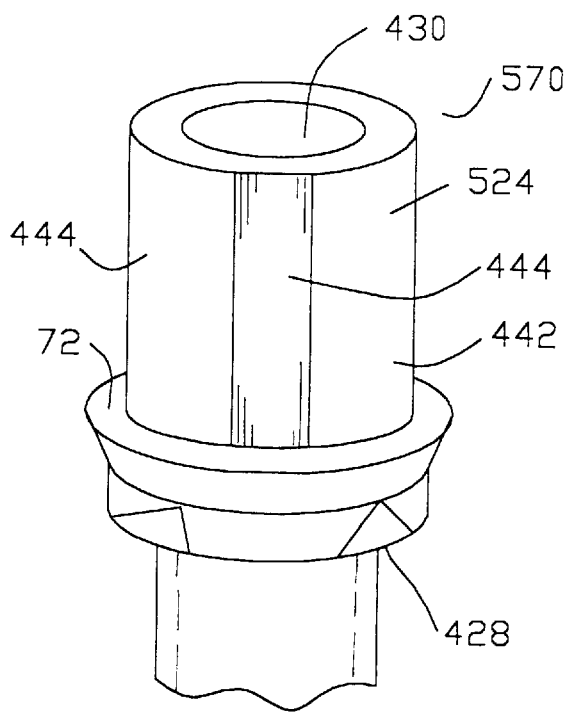

FIGS. 25A and 25B are partial perspective views of implant assemblies 510 and 522. In the embodiment depicted in FIG. 25A, the orifice 426 has a substantially hexagonal shape, and the walls 524 extending from ledge 22 are substantially vertical. In the embodiment depicted in FIG. 25B, the alternating arcuate walls 442 and linear walls 444 form a substantially rectangular shape.

FIGS. 26A–26E illustrate some of the different combinations of elements and shapes which are possible with applicant's invention. FIG. 26A illustrates the cross-sectional configurations of abutment 10, which form ledges 22 and/or 22A in different manners. The various configurations of abutment 10 depicted in FIG. 26A may be combined with the various cross-sectional shapes depicted in FIGS. 26B, 26C, 26D, and 26E.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

Thus, although the top section of the abutment has been illustrated with respect to a hexagon, it will be apparent that other polygonal shapes with alternating arcuate and linear walls also may be used.

Thus, although the preferred embodiment of the abutment has a horizontally-extending ledge disposed beneath the top section of the abutment, it will be apparent that ledges which do not extend horizontally also may be used. Thus, for example, and ledge formed at the intersection of two tapered walls may be used.

Thus, although the preferred embodiment of the abutment is comprised of a base which extend upwardly and outwardly from its bottom to its top, it will be apparent that the base may extend upwardly and inwardly from its bottom to its top, and/or it may extend vertically from its bottom to its top, and/or it may extend upwardly and outwardly and then vertically, and/or it may extend upwardly and inwardly and then vertically, and/or it may extend upwardly and outwardly, and then upwardly and inwardly, and/or it may extend upwardly and inwardly and then upwardly and outwardly.

Thus, although the preferred embodiment of the abutment has a top section formed by alternating linear and arcuate walls, it will be apparent that the top section may be formed by walls which are all linear, by walls which are all arcuate, and by a mixture of these two walls which do not necessarily alternate in configuration.

Thus, the abutment may comprise an interior portion containing from about 3 to about 6 stepped bores, each or all of which may have a circular cross-sectional shape, a polygonal cross-sectional shape, and irregular cross-sectional shape, and the like.

Thus, although the preferred abutment is made from a metal or metal-containing material, the abutment may be made from a ceramic material such as, e.g., aluminum oxide.

I claim:

1. A dental implant assembly comprised of an integral dental implant, wherein said integral dental implant is comprised of an abutment integrally joined to a implant fixture, and wherein:
   (a) said abutment is comprised of a top section, a bottom section integrally joined to said top section, and an orifice extending through a portion of said top section, wherein:
      1. said top section has a cross-sectional shape substantially like a polygon, wherein said shape is formed by alternating linear and arcuate walls,
      2. said abutment is comprised of a ledge disposed beneath said top section of said abutment, and
      3. said abutment is comprised of a wall which extends downwardly and outwardly from its top section.

2. The dental implant assembly as recited in claim 1, wherein said abutment is comprised of said wall which extends downwardly and outwardly from its top section to said ledge, and thereafter extends downwardly and inwardly.

3. The dental implant assembly as recited in claim 2, wherein said assembly is comprised of a drill bit integrally joined to said implant fixture.

4. The dental implant assembly as recited in claim 2, wherein said implant fixture is comprised of a longitudinal channel disposed within the outer surface of said implant fixture.

5. The dental implant assembly as recited in claim 2, wherein said implant fixture is comprised of a substantially cylindrical body portion having raised threads over at least a lower portion thereof.

6. The dental implant assembly as recited in claim 2, wherein said implant assembly is comprised of a healing ball removably attached to said abutment.

7. The dental implant assembly as recited in claim 6, wherein said healing ball is comprised of an orifice extending through the top surface of said healing ball.

8. The dental implant assembly as recited in claim 7, wherein said healing ball consists essentially of plastic.

9. The dental implant assembly as recited in claim 2, wherein an arcuate inwardly-extending groove is disposed between said top section and said bottom section of said abutment.

10. The dental implant assembly as recited in claim 2, wherein said abutment consists essentially of titanium.

11. The dental implant assembly as recited in claim 2, wherein said abutment consists essentially of titanium alloy.

12. The dental implant assembly as recited in claim 1, wherein said abutment is comprised of a multiplicity of cutting flutes.

13. The dental implant assembly as recited in claim 12, wherein said cutting flutes are circumferentially disposed about the periphery of said abutment.

14. The dental implant assembly as recited in claim 1, wherein said implant assembly further comprises a retaining screw disposed within said abutment.

* * * * *